(12) United States Patent
Suzuki et al.

(10) Patent No.: US 8,450,235 B2
(45) Date of Patent: May 28, 2013

(54) SUPPORTED COMPOSITE PARTICLE MATERIAL, PRODUCTION PROCESS OF SAME AND PROCESS FOR PRODUCING COMPOUNDS USING SUPPORTED COMPOSITE PARTICLE MATERIAL AS CATALYST FOR CHEMICAL SYNTHESIS

(75) Inventors: Ken Suzuki, Tokyo (JP); Tatsuo Yamaguchi, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 384 days.

(21) Appl. No.: 12/739,682

(22) PCT Filed: Oct. 23, 2008

(86) PCT No.: PCT/JP2008/069249
§ 371 (c)(1),
(2), (4) Date: Apr. 23, 2010

(87) PCT Pub. No.: WO2009/054462
PCT Pub. Date: Apr. 30, 2009

(65) Prior Publication Data
US 2010/0249448 A1    Sep. 30, 2010

(30) Foreign Application Priority Data
Oct. 26, 2007   (JP) .................. 2007-279397

(51) Int. Cl.
| | | |
|---|---|---|
| *B01J 23/00* | (2006.01) |
| *B01J 23/10* | (2006.01) |
| *B01J 23/40* | (2006.01) |
| *B01J 23/42* | (2006.01) |
| *B01J 23/56* | (2006.01) |
| *B01J 23/58* | (2006.01) |
| *B01J 23/72* | (2006.01) |
| *B01J 23/44* | (2006.01) |
| *B01J 23/02* | (2006.01) |
| *B01J 23/06* | (2006.01) |
| *B01J 23/04* | (2006.01) |
| *B01J 23/70* | (2006.01) |
| *B01J 23/48* | (2006.01) |
| *B01J 23/50* | (2006.01) |
| *B01J 23/08* | (2006.01) |
| *B01J 20/02* | (2006.01) |
| *B01J 20/00* | (2006.01) |
| *B32B 5/16* | (2006.01) |
| *B32B 9/00* | (2006.01) |
| *B32B 15/02* | (2006.01) |
| *B32B 17/02* | (2006.01) |
| *B32B 19/00* | (2006.01) |
| *B32B 21/02* | (2006.01) |
| *B32B 23/02* | (2006.01) |
| *B32B 27/02* | (2006.01) |
| *C07C 69/76* | (2006.01) |
| *C07C 67/00* | (2006.01) |

(52) U.S. Cl.
USPC ........... 502/325; 502/259; 502/262; 502/263; 502/302; 502/303; 502/304; 502/326; 502/327; 502/328; 502/330; 502/331; 502/332; 502/333; 502/334; 502/335; 502/337; 502/339; 502/340; 502/341; 502/344; 502/345; 502/346; 502/347; 502/348; 502/355; 502/406; 502/407; 502/410; 502/411; 502/415; 502/439; 428/403; 560/103; 560/208; 560/238

(58) Field of Classification Search
USPC ......... 502/259, 262, 263, 302–304, 330–335, 502/337, 339–341, 344–348, 355, 406, 407, 502/410, 411, 415, 439, 325–328; 428/403; 560/103, 208, 238
See application file for complete search history.

(56) References Cited

U.S. PATENT DOCUMENTS

| | | | |
|---|---|---|---|
| 3,436,358 A * | 4/1969 | Thygesen | .................. 502/328 |
| 5,347,046 A | 9/1994 | White et al. | |
| 6,103,894 A | 8/2000 | Degelmann et al. | |
| 6,228,800 B1 * | 5/2001 | Yamaguchi et al. | .......... 502/339 |
| 6,514,905 B1 | 2/2003 | Hanaki et al. | |

|         |       |         |                           |
|---------|-------|---------|---------------------------|
| 6,930,073 | B2 * | 8/2005 | Dou .................. 502/328 |
| 7,105,107 | B2 * | 9/2006 | Ramani et al. ......... 252/373 |
| 7,176,159 | B1   | 2/2007 | Wheelock et al. |
| 2001/0025008 | A1 | 9/2001 | Hu et al. |
| 2003/0040635 | A1 | 2/2003 | Jansen et al. |
| 2003/0060655 | A1 | 3/2003 | Hayashi et al. |
| 2006/0084830 | A1 | 4/2006 | Ryu |
| 2007/0179320 | A1 | 8/2007 | Hirota et al. |
| 2011/0184206 | A1 * | 7/2011 | Suzuki et al. ......... 560/103 |

FOREIGN PATENT DOCUMENTS

|    |               |         |
|----|---------------|---------|
| CN | 1123527 A     | 5/1996  |
| CN | 1915475 A     | 2/2007  |
| EP | 1 283 206 A2  | 2/2003  |
| EP | 1 459 803 A1  | 9/2004  |
| EP | 1 495 802 A1  | 1/2005  |
| GB | 1 415 636 A   | 11/1975 |
| JP | 62-27041      | 2/1987  |
| JP | 07-047273     | 2/1995  |
| JP | 07-313880     | 12/1995 |
| JP | 8-57323       | 3/1996  |
| JP | 11-1490       | 1/1999  |
| JP | 2000-154164   | 6/2000  |
| JP | 2001-79402    | 3/2001  |
| JP | 2002-282876   | 10/2002 |
| JP | 2002-361086   | 12/2002 |
| JP | 2003-53188    | 2/2003  |
| JP | 2003-103174   | 4/2003  |
| JP | 2003-521364   | 7/2003  |
| JP | 2004-351364   | 12/2004 |
| JP | 2007-197396   | 8/2007  |
| JP | 2006-240920   | 9/2008  |
| WO | WO 2004/011138 A1 | 2/2004 |
| WO | WO 2006/079850 A1 | 8/2006 |

OTHER PUBLICATIONS

"Preparation of Ag-NiO Composite Powders by Spray Pyrolysis from AG and Ni Loading Versatic Acid 10", Akihiko Okuda et al. Resources and Materials, vol. 118 (2002), pp. 91-94.*

"Theoretical optical properties of composite metal-NiO films," F. F. Ferreira et al. Journal of Physics D: Applied Physics 36 (2003), pp. 2386-2392.*

Office Action for Chinese Application No. 200880112821.7 dated Feb. 22, 2012.

P. Castano et al, "Enhancement of pyrolysis gasoline hydrogenation over Pd-promoted Ni/$SiO_2$-$Al_2O_3$ catalysts," Fuel 86, pp. 2262-2274, (2007).

European Search Report for Corresponding EP Application No. 08841939.5-1270 dated Nov. 17, 2011.

International Preliminary Report on Patentability dated Jun. 10, 2010 in PCT/JP2008/069249.

Nakawa et al., "Oxidation With Nickel Peroxide. I. Oxidation of Alcohols," The Journal of Organic Chemistry, vol. 27, No. 5, pp. 1597-1601, (1962).

Choudary et al., "The First Example of Activation of Molecular Oxygen by Nickel in Ni-Al Hydrotalcite: A Novel Protocol for the Selective Oxidation of Alcohols," Angew, Chem. Int. Ed., vol. 40, No. 4, pp. 763-766, (2001).

Kawabata et al., "Nickel Containing Mg-Al Hydrotalcite-Type Anionic Clay Catalyst for the Oxidation of Alcohols With Molecular Oxygen," Journal of Molecular Catalysis A: Chemical, vol. 236, pp. 206-215, (2005).

Ji et al., "Simple Fabrication of Nano-Sized $NiO_2$ Powder and Its Application to Oxidation Reactions," Applied Catalysis A: General, vol. 282, pp. 25-30, (2005).

International Search Report from the Japanese Patent Office for International Application No. PCT/JP2008/069249 (Mar. 3, 2009).

Grisel, R.J.H. et al., "A Comparative Study of the Oxidation of CO and $CH_4$ Over Au/$MO_x$/$Al_2O_3$ Catalysts," Catalysis Today 64 (2001) 69-81.

Office Action for CN Application No. 200880112821.7 mailed Nov. 27, 2012.

Barrio, V.L. et al., "Evaluation of Silica-Alumina-Supported Nickel Catalysts in Dibenzothiophene Hydrodesulphurisation," Applied Catalysts A: General 248 (2003) 211-225.

Office Action for TW Application No. 097140722 mailed Sep. 27, 2012.

* cited by examiner

*Primary Examiner* — Patricia L Hailey

(74) *Attorney, Agent, or Firm* — Finnegan, Henderson, Farabow, Garrett & Dunner, L.L.P.

(57) ABSTRACT

A supported composite particle material comprises: a composite particle formed of an oxidized nickel and X (wherein X represents at least one of elements selected from the group consisting of nickel, palladium, platinum, ruthenium, gold, silver and copper); and a support on which the composite particle is supported, the supported composite particle material having a supported layer in which the composite particle is localized.

15 Claims, 4 Drawing Sheets

US 8,450,235 B2

SUPPORTED COMPOSITE PARTICLE MATERIAL, PRODUCTION PROCESS OF SAME AND PROCESS FOR PRODUCING COMPOUNDS USING SUPPORTED COMPOSITE PARTICLE MATERIAL AS CATALYST FOR CHEMICAL SYNTHESIS

TECHNICAL FIELD

The present invention relates to a supported composite particle material in which composite particle formed of an oxidized nickel and X (wherein X represents at least one type of elements selected from the group consisting of nickel, palladium, platinum, ruthenium, gold, silver and copper) is supported onto a support, a process for producing the supported composite particle material, and a process for producing compounds, using the supported composite particle material as a catalyst for chemical synthesis.

BACKGROUND ART

Nickel or nickel compounds are widely used as catalysts for chemical synthesis such as in oxidation reactions, reduction reactions, hydrogenation reactions or the like. Conventional examples of the use of nickel or nickel compounds in oxidation reactions may include: (1) an alcohol oxidation reaction in which nickel peroxide ($NiO_2$) is used as a stoichiometric oxidizing agent (Non-Patent Document 1), (2) an alcohol aerobic oxidation reaction using Ni—Al hydrotalcite as a catalyst (Non-Patent Document 2), (3) an alcohol aerobic oxidation reaction using Mg—Al hydrotalcite containing Ni(II) as a catalyst (Non-Patent Document 3), and (4) an alcohol aerobic oxidation reaction using nickel peroxide ($NiO_2$) nanoparticles as a catalyst (Non-Patent Document 4).

As described in (1) above, highly oxidized nickel peroxide has a higher level of oxidizing power than nickel oxide, and has long been known to be able to oxidize various alcohols stoichiometrically. This type of nickel peroxide has not been obtained in pure form or in the form of an anhydride, there are many aspects of its structure that remain unclear, and is also said to be a nickel oxide that has adsorbed oxygen. However, since nickel peroxide is extremely useful as a stoichiometric oxidizing agent, if it were possible to catalytically generate active oxidizing active species using moleculer oxygen for the oxidizing agent, it would be able to be applied to aerobic oxidation of numerous organic substrates.

Catalytic alcohol aerobic oxidation reactions have been realized in recent years as a result of various modifications and improvements to nickel-based catalysts. The nickel-hydrotalcite-based catalysts described in (2) and (3) above realize highly efficient activation of moleculer oxygen by compounding Ni with dissimilar metal elements (such as Al or Mg), thereby achieving aerobic oxidation with a heterogeneous nickel catalyst. In these catalysts, Ni functions as an oxygen activation site as a result of compounding Ni with a dissimilar metal element, and is thought to result in the formation of peroxo species serving as reactive species on the Ni. In addition, in the method described in (4) above using nickel peroxide, the reaction has been reported to proceed catalytically as a result of forming the nickel oxide into nanoparticles.

In the chemical industry, the use of nickel and nickel compounds is not limited to alcohol oxidation reactions, but have also been shown to be widely effective in various reactions such as various oxidation reactions, reduction reactions and hydrogenation reactions, as well as in catalysts for purification of automobile exhaust gas and in photocatalysts.

Non-Patent Document 1: J. Org. Chem., 27 (1962) 1597
Non-Patent Document 2: Angew. Chem. Int. Ed., 40 (2001) 763
Non-Patent Document 3: J. Mol. Catal., A236 (2005) 206
Non-Patent Document 4: Appl. Catal., A282 (2005) 25

DISCLOSURE OF THE INVENTION

Problems to be Solved by the Invention

However, the known methods described above do not necessarily have adequate target product selectivity or catalyst activity, and are unlikely to be considered as industrially advantageous methods. In addition, in consideration of the objective of realizing a reduction in the amount of active ingredient used and high reactivity, nickel and nickel compounds used as catalysts are generally used by dispersing and supporting onto a support in order to increase specific surface area and enhance usage efficiency during use as catalyst components. Although supports on which nickel or nickel compounds are supported are of various types depending on reaction characteristics and application, these supports have problems such as not always being able to obtain satisfactory reaction activity or catalyst active ingredients being susceptible to dropout from the support depending on the distribution of catalyst components within the support.

The present inventors conducted extensive studies on the supported composite particle material of the present application, in which composite particles comprising oxidized nickel and X (wherein X represents at least one of elements selected from the group consisting of nickel, palladium, platinum, ruthenium, gold, silver and copper) are supported onto a support, based on the premise of practical application thereof in an industrial process. As a result, in the case of using as a catalyst for chemical synthesis, since a supported composite particle material in which composite particles are uniformly supported on the inside of a support inhibit diffusion of reaction raw materials and reaction products due to the resistance of pores inside the support, composite particles supported inside a support are not used effectively, and such supported composite particle material has been clearly demonstrated to prevent the obtaining of catalysts that are not necessarily satisfactory from the viewpoint of reaction activity. In addition, the composite particles supported onto the outer surface of support particles were determined to have problems such as a loss of activity due to concealment of active sites due to the adsorption of reaction by-products and accumulation of toxic substances depending on the type of reaction or type of reaction apparatus and the like, and a loss of catalyst activity due to composite particles dropping out from the support due to wear caused by collisions between support particles and between support particles and reactor walls and the like.

With the foregoing in view, an object of the present invention is to provide a supported composite particle material that maintains high reactivity for a long period of time by stably supporting composite particles comprised of an oxidized nickel and X (wherein X represents at least one of elements selected from the group consisting of nickel, palladium, platinum, ruthenium, gold, silver and copper) on a support, a process for producing the supported composite particle material, and a process for producing compounds using the supported composite particle material as a catalyst for chemical synthesis.

Means for Solving the Problems

As a result of conducting extensive studies on the above-mentioned problems, the present inventors found that, in a supported composite particle material comprising composite particles comprised of an oxidized nickel and X (wherein X represents at least one of elements selected from the group consisting of nickel, palladium, platinum, ruthenium, gold, silver and copper) and a support on which the composite particles are supported, by controlling the distribution of the composite particles within the support and forming a supported layer in which the composite particles are localized within a specific range, the above-mentioned problems can be resolved, thereby leading to completion of the present invention.

Namely, the present invention is as described below:

[1] A supported composite particle material comprising:

a composite particle formed of an oxidized nickel and X (wherein X represents at least one of elements selected from the group consisting of nickel, palladium, platinum, ruthenium, gold, silver and copper); and a support on which the composite particle is supported, wherein the supported composite particle material comprises a supported layer in which the composite particle is localized.

[2] The supported composite particle material according to item [1], wherein the supported layer in which the composite particle is localized is present in a region extending from a surface of the supported composite particle material to 40% of an equivalent diameter of the supported composite particle material.

[3] The supported composite particle material according to item [1] or [2], wherein the equivalent diameter of the supported composite particle material exceeds 200 μm, and the supported layer in which the composite particle is localized is present in a region extending by 80 μm from an outer surface of the supported composite particle material.

[4] The supported composite particle material according to item [1] or [2], wherein the equivalent diameter of the supported composite particle material is 200 μm or less, and the supported layer in which the composite particle is localized is present in a region extending from the surface of the supported composite particle material to 30% of the equivalent diameter of the supported composite particle material.

[5] The supported composite particle material according to any one of items [1] to [4], comprising an outer layer substantially free of the composite particle on an outside of the supported layer in which the composite particle is localized.

[6] The supported composite particle material according to item [5], wherein the outer layer is formed at a thickness of 0.01 to 15 μm from the outer surface of the support.

[7] The supported composite particle material according to any one of items [1] to [6], wherein the composite particle has a mean particle diameter of from 2 to 10 nm.

[8] The supported composite particle material according to any one of items [1] to [7], wherein a compositional ratio of nickel and X in the composite particle, in terms of an atomic ratio of Ni/X, is from 0.1 to 10.

[9] The supported composite particle material according to any one of items [1] to [8], wherein the composite particle has a core formed of X and the core is coated with oxidized nickel.

[10] The supported composite particle material according to any one of items [1] to [9], wherein the support is formed of an aluminum-containing silica-based composition containing silica and alumina.

[11] A process for producing a supported composite particle material in which the composite particle formed of an oxidized nickel and X (wherein X represents at least one of elements selected from the group consisting of nickel, palladium, platinum, ruthenium, gold, silver and copper) is supported onto a support, comprising:

a first step of obtaining a mixture at a temperature of at least 60° C. by mixing an aqueous slurry containing a support on which is supported an oxide of at least one of basic metals selected from the group consisting of alkaline metals, alkaline earth metals and rare earth metals, and an acidic aqueous solution of a soluble metal salt containing nickel and the X; and a second step of heat-treating a precursor contained in the mixture.

[12] The process for producing the supported composite particle material according to item [11], wherein the aqueous slurry further comprises a salt of at least one of basic metals selected from the group consisting of alkaline metals, alkaline earth metals and rare earth metals.

[13] The process for producing the supported composite particle material according to item [11] or [12], wherein the aqueous slurry further comprises a soluble aluminum salt.

[14] A process for producing carboxylic acid ester comprising:

reacting an aldehyde and an alcohol in the presence of oxygen by using the supported composite particle material according to any one of items [1] to [10] as a catalyst.

[15] The process for producing carboxylic acid ester according to item [14], wherein the aldehyde is selected from acrolein, methacrolein or a mixture thereof.

[16] The process for producing carboxylic acid ester according to item [14] or [15], wherein the alcohol is methanol.

Advantageous Effects of the Invention

The supported composite particle material according to the present invention is able to maintain high reactivity over a long period of time by efficiently using composite particles by stably supporting composite particles comprised of the oxidized nickel and X (wherein X represents at least one of elements selected from the group consisting of nickel, palladium, platinum, ruthenium, gold, silver and copper) on a support.

BEST MODE FOR CARRYING OUT THE INVENTION

Figure 1:
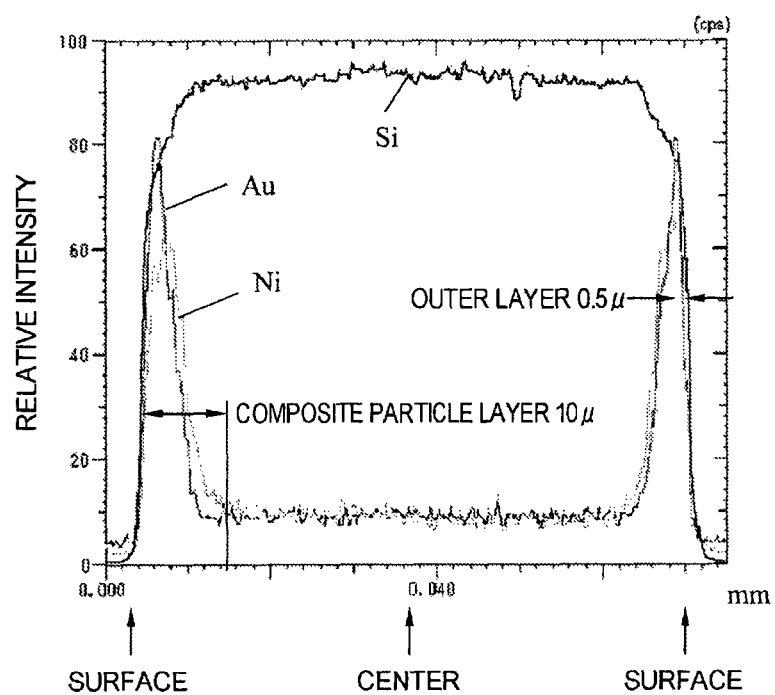
FIG. 1 shows the results of X-ray analysis using an X-ray microprobe of a particle cross-section of the supported composite particle material of Example 1.

The following provides an explanation of the best mode for carrying out the present invention (to be referred to as "the present embodiment"). The following embodiment is exemplified for explaining the present invention, and is not intended to limit the present invention to only this embodiment. The present invention can be carried out in various forms without deviating from the gist thereof.

[Supported Composite Particle Material]

The supported composite particle material according to the present embodiment comprises composite particles comprised of an oxidized nickel and X (wherein X represents at least one of elements selected from the group consisting of nickel, palladium, platinum, ruthenium, gold, silver and copper) and a support on which the composite particles are supported, and has a supported layer in which the composite particle is localized.

The term "supported layer in which the composite particles are localized" used herein refers to a region in the support in which the composite particles are concentrated. In the supported composite particle material according to the present embodiment, since the composite particles are not randomly supported in the support, but rather selectively supported in a fixed region, this region is generically referred to as a "supported layer in which the composite particles are localized". In the supported composite particle material, since a region is a "supported layer in which the composite particles are localized" provided the composite particles are concentrated in a fixed region as compared with other portions, which region is a "supported layer in which the composite particles are localized" can be determined by X-ray microprobe analysis to be described later or from secondary electron reflected images obtained with a high-resolution scanning electron microscope. The supported layer in which the composite particles are localized is preferably present in a region extending from the surface of the supported composite particle material to 40% of the equivalent diameter of the supported composite particle material. If the supported layer in which the composite particles are localized is present in this region, the effects of diffusion rates of the reactants within the support are reduced, which tends to improve reaction activity.

The supported composite particle material according to the present embodiment can have various sizes and various shapes such that the substantial thickness of particle diameter is on the μm to cm order. Specific examples of the shape of the supported composite particle material may include various shapes such as spheres, ovals, cylinders, tablets, hollow cylinders, plates, rods, sheets, honeycombs or the like. The shape of the supported composite particle material can be suitably changed according to the reaction form, and in a fixed bed reaction, for example, hollow cylindrical or honeycomb-shaped particles are selected due to their low pressure loss, while spherical particles are typically selected under conditions of suspending in a liquid phase slurry.

The term "equivalent diameter" used herein refers to the diameter of spherical particles, or in the case of irregularly shaped particles, the diameter of a sphere having an equal volume as the particles or having a surface area equal to the surface area of the particles. Equivalent diameter is measured by measuring the mean particle diameter (volume-based) using a laser diffraction/scattering particle size distribution measuring apparatus and using the resulting value as the equivalent diameter. Alternatively, number average particle diameter as measured with a scanning electron microscope (SEM) can also be used to represent equivalent diameter.

The thickness of the supported layer in which the composite particles are localized is selected to an optimum range according to the thickness of the support, particle diameter, type of reaction and reaction form. Furthermore, since the "equivalent diameter of the supported composite particle material" is usually the same as the "equivalent diameter of the support", the "equivalent diameter of the supported composite particle material" can be determined from the equivalent diameter of the support.

For example, in the case of using a support of a size such that the thickness of the support exceeds 200 μm (for example several mm or more), the supported composite particle material is generally used in a liquid phase reaction having a comparatively slow reaction rate or in a vapor phase reaction. Thus, by providing a region in which the active component in the form of composite particles extend from the surface of the supported composite particle material to 40% of the equivalent diameter of the supported composite particle material, and a layer in which the composite particles are supported to 80 μm from the outer surface of the supported composite particle material but not supported inside the supported composite particle material, the supported composite particle material can be obtained that is resistant to the effects of the diffusion rates of the reactants. As a result, the composite particles can be used effectively.

On the other hand, in the case the thickness of the support is 200 μm or less, the composite particles are preferably supported in a region extending from the surface of the supported composite particle material to 30% of the equivalent diameter of the supported composite particle material. In the case of using in a liquid phase reaction in particular, the support was conventionally designed to have a small particle diameter in line with the reaction due to the effects of the reaction rate and the intrapore diffusion rates of reactants within the support. In the present embodiment, a highly active supported composite particle material can be obtained without reducing the particle diameter of the support by reducing the thickness of the supported layer in which the composite particles are localized. Namely, according to the present embodiment, it becomes easy to separate the catalyst by settling, thereby resulting in the advantage of enabling separation to be carried out using a small-volume separator. However, if the volume of the portion of composite particles in the supported composite particle material that are not supported becomes excessively large, the volume not required by the reaction per container increases, thereby resulting in waste. Thus, it is preferable to set the particle diameter of the support, the required thickness of the supported layer in which composite particles are localized and the thickness of the layer in which composite particles are not supported according to the reaction form.

The supported composite particle material may also have an outer layer substantially free of composite particles on the outside of the supported layer in which composite particles are localized. The outer layer is preferably formed at a thickness of 0.01 to 15 μm from the outer surface of the support. As a result of providing the outer layer within this range, the supported composite particle material can be used as a catalyst strongly resistant to catalyst poisoning that inhibits the loss of composite particles due to abrasion in reactions using reactors such as a fluidized bed, bubble column, stirring reactor or other reactor for which there is the risk of friction of catalyst particles, and in reactions in which there is accumulation of catalytic poisons. In addition, since the outer layer can be controlled to be extremely thin, large decreases in activity can be suppressed.

The thickness of the outer layer substantially free of composite particles is selected to an optimum range according to the reaction characteristics, physical properties of the support, loading of composite particles and the like, and is preferably from 0.01 to 15 μm, more preferably from 0.1 to 10 μm, and even more preferably from 0.2 to 5 μm. If the thickness of the outer layer (composite particle-non-supported layer) exceeds 15 μm, although there is no change in the effect of improving catalyst life when using the composite particles as a catalyst, this leads to a decrease in catalyst activity. If the thickness of the outer layer is less than 0.01 μm, susceptibility to loss of catalyst particles due to abrasion tends to increase.

In the present embodiment, the term "substantially free of composite particles" used herein refers to the substantial absence of a peak indicating the distribution oxidized nickel and X (wherein X represents at least one of elements selected from the group consisting of nickel, palladium, platinum, ruthenium, gold, silver and copper) having a relative intensity of 10% or more in X-ray microprobe analysis to be described later or in secondary electron reflected images obtained with a high-resolution scanning electron microscope.

The composite particles of the present embodiment are particles comprised of an oxidized nickel and X (wherein X represents at least one of elements selected from the group consisting of nickel, palladium, platinum, ruthenium, gold, silver and copper).

Preferable examples of the oxidized nickel may include nickel oxides formed by bonding nickel and oxygen (such as $Ni_2O$, $NiO$, $NiO_2$, $Ni_3O_4$ or $Ni_2O_3$), and composite oxides containing nickel such as nickel oxide compounds formed by bonding nickel and X and/or one or more types of other metal elements and oxygen, or a solid solution or mixture thereof.

The term "nickel oxide" used herein refers to a compound containing nickel and oxygen. Nickel oxides may include the previously exemplified $Ni_2O$, $NiO$, $NiO_2$, $Ni_3O_4$ or $Ni_2O_3$ or hydrates thereof, hydroperoxides of nickel containing an OOH group, peroxides of nickel containing an $O_2$ group, and mixtures thereof.

In addition, the term "composite oxide" used herein refers to an oxide containing two or more types of metals. The term "composite oxide" used herein refers to an oxide in which two or more types of metal oxides form a compound, and although it includes multiple oxides not containing an ion of an oxoacid as a structural unit (such as pervoskite oxides and spinel oxides of nickel), it refers to that having a broader context than multiple oxides, and includes all oxides in which two or more types of metals are compounded. Oxides in which two or more types of metal oxides form a solid solution are also within the scope of composite oxides.

The present inventors found that, in the case of using the supported composite particle material according to the present embodiment as a catalyst for synthesis of carboxylic acid esters, by compounding nickel oxide with X, the inherent catalytic ability of nickel oxides having oxidative esterification activity can be brought out and a remarkably high level of catalyst performance can be demonstrated unlike that realized with a catalyst comprised of each component alone. This is thought to be a unique effect demonstrated as a result of compounding a nickel compound and X that is the result of a novel catalyst action completely different from that demonstrated by each component alone due to a dual functional effect between both metal components or the formation of a new active species. On the basis of this novel concept, in the case of supporting oxidized nickel and X on a support in a highly dispersed state, astonishing catalyst performance unable to be obtained with conventional catalysts was able to be realized.

For example, if gold is selected for X and nickel oxide and gold are supported onto a support in a highly dispersed state, remarkably high catalyst performance appears. This catalyst was observed to demonstrate a high degree of carboxylic acid ester selectivity and a considerable improvement in activity at a specific composite ratio of Ni/Au as compared with respectively supporting nickel oxide or gold alone onto a support. The catalyst also demonstrates high catalytic activity per metal atom as compared with support particles comprised of each component alone, and the appearance of catalyst performance as a result of their compounding is strongly dependent on the supported composition of nickel and gold. This is presumed to be due to the presence of an optimum ratio for the formation of a nickel oxidation state that is optimum for the reaction. In this manner, highly prominent compounding effects, which cannot be predicted from the simple combined addition of each component alone, are demonstrated as a result of dispersing two components comprising the nickel oxide and gold and supporting onto a support.

The supported composite particle material in which gold is selected for X have the oxidized nickel and gold supported onto a support in a highly dispersed state, and both components have been observed to be compounded at the nanometer level. Based on the results of transmission electron microscope/scanning transmission electron microscope (TEM/STEM) observations, nearly spherical nanoparticles measuring 2 to 3 nm are uniformly dispersed and supported on a support. According to an elementary analysis of the nanoparticles by energy dispersive X-ray spectrometry (EDS), all of the particles were observed to contain nickel and gold, and the nickel was observed to be coating the surface of gold nanoparticles. In addition, a nickel component alone was also observed to be supported onto the support in addition to the nanoparticles containing nickel and gold.

According to the results of X-ray photoelectron spectroscopy (XPS) and powder X-ray diffraction (XRD), although gold is present in the form of a crystalline metal, nickel is presumed to be present in the form of an amorphous oxide having a bivalence.

On the basis of ultraviolet-visible spectroscopy (UV-Vis), a surface plasmon absorption peak (at about 530 nm) originating from gold nanoparticles observed in gold nanoparticles of a single metal species was determined to disappear when nickel oxide and gold were compounded. The phenomenon involving disappearance of this surface plasmon absorption peak was not observed in catalysts comprised of combinations of gold and metal oxide species other than nickel oxide not observed to have an effect on the reaction (including metal oxides such as chromium oxide, manganese oxide, iron oxide, cobalt oxide, copper oxide or zinc oxide). The disappearance of this surface plasmon absorption peak is thought to be the result of the formation of a mixed electron state mediated by the contact interface between oxidized nickel and gold, or in other words, the result of hybridization of two types of metallic chemical species.

Conversion to highly oxidized nickel oxide can be confirmed by a color change of a catalyst and ultraviolet-visible spectroscopy (UV-Vis). As a result of adding gold to nickel oxide, the nickel oxide changed in color from grayish green to brown, and the UV spectrum demonstrated absorbance over nearly the entire visible light region. The shape of the UV spectrum and the color of the catalyst were similar to that of highly oxidized nickel oxide ($NiO_2$) measured as a reference sample. On the basis of this finding, nickel is presumed to be converted to a highly oxidized nickel oxide by the addition of gold.

On the basis of the above results, the structure of the composite particles in the case of selecting gold for X is believed to be such that the gold particles serve as the core and the surface thereof is coated with highly oxidized nickel oxide, without any gold atoms present on the surface of the composite particles.

The supported composition of nickel and X onto a support is preferably within a range of from 0.20 to 0.99, more preferably within a range of from 0.30 to 0.90, and even more preferably within a range of from 0.50 to 0.90, in terms of the atomic ratio of Ni/(Ni+X). The term "atomic ratio of Ni/(Ni+X)" used herein refers to a ratio of the number of atoms of nickel supported onto the support to the total number of atoms of nickel and X.

The composite particles are preferably supported onto the support in a highly dispersed state. The composite particles are more preferably supported by being dispersed in the form of microparticles or a thin film, and the mean particle diameter thereof is preferably from 2 to 10 nm, more preferably from 2 to 8 nm, and even more preferably from 2 to 6 nm.

If the mean particle diameter of the composite particles is within the above ranges, a specific active species structure comprised of nickel and X is formed and reaction activity tends to improve. Here, mean particle diameter in the present embodiment refers to the number average particle diameter as measured with a transmission electron microscope (TEM). More specifically, in an image observed with a transmission electron microscope, area of black contrast indicate composite particles, and the mean particle diameter thereof can be calculated by measuring the diameter of each particle for all particles.

The composition of nickel and X in the composite particles is preferably within a range of from 0.1 to 10, more preferably within a range of from 0.2 to 5.0 and even more preferably within a range of from 0.3 to 3.0 in terms of the atomic ratio of Ni/X. If the atomic ratio of Ni/X is within the above ranges, a specific active species structure comprised of nickel and X and a nickel oxidized state optimum for the reaction are formed, and as a result thereof, activity and selectivity tend to be higher than a supported composite particle material comprised of nickel and X outside the above ranges.

Although there are no particular limitations on the form of the composite particles provided both of the components of nickel and X are contained therein, preferably both components are present in the particles, and the particles are in a form having a phase structure, such as a solid solution structure in which chemical species randomly occupy crystal sites, a core-shell structure in which each chemical species is separated in the shape of concentric spheres, a anisotropic phase separation structure in which phases are separated anisotropically, or a heterobondphilic structure in which both chemical species are present adjacent to each other on the particle surface. More preferably, the composite particles have a form in which they have a core comprised of X and oxidized nickel is coated onto the surface of the cores. There are no particular limitations on the shape of the composite particles provided both components are contained therein, and the shape may be spherical or hemispherical and the like.

As previously described, transmission electron microscopy/scanning transmission electron microscopy (TEM/STEM), for example, is effective as an analysis technique for observing the form of the composite particles, and elementary analyses within the particles and extraction of images of the distribution of elements therein are possible by irradiating nanoparticles observed by TEM/STEM with an electron beam. The composite particles of the present embodiment contain nickel and X in all of the particles thereof as will be indicated in the examples to be described later, and have been confirmed to have a form in which the surface of X is coated with nickel. In the case of having such a form, the atomic ratio of nickel and X varies according to the locations of the composition analysis points in the particles, and nickel is detected in larger amounts on the edges of the particles than in the central portion thereof. Thus, there are variations in the atomic ratio of nickel and X depending on the locations of the analysis points even among individual particles, and the range thereof is included in the range of the atomic ratio of Ni/X as previously described.

In the case of having selected gold, silver or copper for X, ultraviolet-visible spectroscopy (UV-Vis) is an effective means of identifying the structure thereof. In the case of nanoparticles of gold, silver or copper alone, coupling occurs between the photoelectric field of the visible to near infrared region and free electrons on the surface of the metal resulting in the occurrence of surface plasmon absorption. For example, when a catalyst supported with gold particles is irradiated with visible light, an absorption spectrum is observed that is based on plasmon resonance originating from gold particles at a wavelength of about 530 nm. However, in the supported composite particle material in which nickel oxide and gold are supported according to the present embodiment, since the surface plasmon absorption thereof disappears, gold can be considered to not be present on the surface of the composite particles of the present embodiment.

There are no particular limitations on the solid form of the nickel provided the prescribed activity is obtained, and is preferably in an amorphous form in which diffraction peaks are not observed in X-ray diffraction. As a result of having such a form, in the case of using as a catalyst of an oxidation reaction, interaction with oxygen is presumed to increase, and since the bonding interface between the oxidized nickel and X increases, even better activity tends to be obtained.

In the present embodiment, X is at least one of elements selected from the group consisting of nickel, palladium, platinum, ruthenium, gold, silver and copper, and is more preferably selected from the group consisting of nickel, palladium, ruthenium, gold and silver.

Although the chemical state of X may be a metal, an oxide, an hydroxide, a composite oxide containing X and nickel or one or more types of another metal element, or a mixture thereof, the chemical state of X is preferably a metal or oxide, and more preferably a metal. In addition, there are no particular limitations on the solid form of X provided the prescribed activity is obtained, the form may be either a crystalline form or an amorphous form.

The term "another metal element" used herein refers to a constituent element of a support to be described later, a third component other than oxidized nickel and X contained in the supported composite particle material, or a metal component such as an alkaline metal, alkaline earth metal or rare earth metal.

The supported composite particle material according to the present embodiment has oxidized nickel and X supported onto a support as previously described, and demonstrates superior effects as a result of forming composite particles comprised of oxidized nickel and X. Furthermore, the term "composite particle" used herein refers to a particle containing different binary metal species in a single particle. Examples of different binary metal species may include binary metal particles in which both the nickel and X are metals and metal particles forming an alloy or intermetallic compound of nickel and X, and the case of using these as catalysts for chemical synthesis, the selectivity of the target product and the activity of the catalyst tend to be lower than the supported composite particle material according to the present embodiment.

The supported composite particle material according to the present embodiment preferably contains oxidized nickel alone on the support in addition to the composite particles comprised of oxidized nickel and X. The presence of oxidized nickel not compound with X further enhances the structural stability of the supported particles, and inhibits increases in pore diameter caused by prolonged reactions as well as the accompanying growth of the composite particles. This effect is particularly remarkable in the case of using an aluminum-containing silica-based composition containing silica and alumina for the support as will be described later.

The following provides an explanation of mechanism that enhances structural stability of the supported composite particle material and that inhibits increases in pore diameter caused by prolonged reactions as well as the accompanying growth of composite particles by having oxidized nickel alone present on a support.

As will be described later, in a synthesis reaction of a carboxylic acid ester, by adding a compound of an alkaline metal or alkaline earth metal to the reaction system to maintain a pH of the reaction system at 6 to 9, and more preferably to neutral conditions (for example, pH 6.5 to 7.5), namely as close to pH 7 as possible, it is possible to inhibit the production of acetals and other by-products caused by acidic substances exemplified by methacrylic acid or acrylic acid that are unique by-products of carboxylic acid ester production reactions.

According to studies conducted by the present inventors, in the case of carrying out a prolonged reaction according to the reaction procedure described above using a supported gold particle material in which single-component gold particles are supported onto a support comprised of an aluminum-containing silica-based composition containing silica and alumina, structural changes were determined to occur, although gradually, in the supported gold particle material. This phenomenon is thought to be caused by an increase in pore diameter of the supported particle material due to the supported particle material being locally and repeatedly exposed to acid and base causing a portion of the Al in the support to dissolve and precipitate and resulting in rearrangement of the silica-alumina crosslinked structure. In addition, accompanying changes causing an increase in pore diameter, sintering of the gold particles occurs, and this was determined to lead to a decrease in catalyst activity due to a decrease in surface area.

On the other hand, the presence of composite particles and oxidized nickel alone on the support enhanced the structural stability of the supported particle material according to the reaction procedure described above, thereby inhibiting increases in pore diameter and growth of the composite particles. As was previously described, the formation of nickel oxide compounds or composite oxides containing nickel in the form of a solid solution and the like as result of oxidized nickel reacting with constituent elements of the support is considered to be factor behind the reason for this, and as a result of such nickel compounds acting to stabilize the silica-alumina crosslinked structure, structural changes in the supported particle material are thought to have greatly improved. The present inventors presumed that the appearance of this support structure stabilizing effect is attributable to the oxidized nickel present in the support. Consequently, although this effect is naturally obtained in the case oxidized nickel contained in composite particles is in contact with the support, even greater stabilizing effects are thought to be obtained in the case oxidized nickel is present alone on the support.

There are no particular limitations on the support of the supported composite particle material according to the present embodiment provided oxidized nickel and X can be supported onto the support, and conventional catalyst supports used for chemical synthesis can be used.

Examples of supports may include various types of supports such as activated charcoal, silica, alumina, silica-alumina, titania, silica-titania, zirconia, magnesia, silica-magnesia, silica-alumina-magnesia, calcium carbonate, zinc oxide, zeolite, crystalline metallosilicate or the like. Preferable examples of supports may include activated charcoal, silica, alumina, silica-alumina, silica-magnesia, silica-alumina-magnesia, titania, silica-titania and zirconia. More preferable examples may include silica-alumina and silica-alumina-magnesia.

In addition, one or a plurality of types of metal components selected from the group consisting of alkaline metals (Li, Na, K, Rb or Cs), alkaline earth metals (Be, Mg, Ca, Sr or Ba) and rare earth metals (La, Ce or Pr) may be contained in the support. Metal components that become oxides as a result of firing, such as nitrates or acetates, are preferably used for the metal components supported onto the support.

A support comprised of an aluminum-containing silica-based composition containing silica and aluminum is preferably used for the support. The support has higher water resistance than silica and higher acid resistance than alumina. In addition, the support is provided with properties superior to supports typically used in the prior art, including greater hardness and higher mechanical strength than activated charcoal, and is also able to stably support the active components in the form of oxidized nickel and X. As a result, the reactivity of the supported composite particle material can be maintained over a long period of time.

The supported composite particle material having a specific atomic ratio for oxidized nickel and X and using an aluminum-containing silica-based composition for the support has high mechanical strength, is physically stable and satisfies corrosion resistance with respect to liquid properties unique to the reaction despite having a large surface area suitable for use as a catalyst support in the case of using as a catalyst for chemical synthesis.

The following provides an explanation of the characteristics of a support comprised of an alumina-containing silica-based composition containing silica and alumina of the present embodiment capable of considerably improving catalyst life. Reasons for being able to greatly improve the mechanical strength and chemical stability of the support are as described below.

The support comprised of an aluminum-containing silica-based composition contains newly formed Si—O—Al—O—Si bonds resulting from the addition of aluminum (Al) to a non-crosslinked silica (Si—O) chain of a silica gel, and as a result of an Al-crosslinked structure having been formed without any loss of the inherent stability to acidic substances of the Si—O chain, it is thought that the Si—O bonds are strengthened, thereby resulting in a considerable improvement in the stability of hydrolysis resistance (to be simply referred to as "water resistance"). In addition, when a Si—O—Al—O—Si crosslinked structure is formed, the number of non-crosslinked Si—O chains decreases in comparison with the case of silica gel alone, and this is thought to increase mechanical strength. Namely, there is presumed to be a correlation between the number of Si—O—Al—O—Si structures formed and improvement of the mechanical strength and water resistance of the resulting silica gel.

One of the reasons for it being possible to stably support the oxidized nickel and X on a support for a long period of time is that the mechanical strength and chemical stability of the support are greatly improved as previously described, enabling it to be provided with superior physical properties in comparison with typically used supports of the prior art. As a result, it is difficult for the active components in the form of nickel and X to separate from the support, which is thought to enable the nickel and X to be stably supported over a long period of time.

In the case of typically used supports such as silica or silica-titania, nickel components are observed to elute from the support, although gradually, in prolonged reactions. In contrast, in the case of using the support described above, the present inventors found that elution of nickel components is suppressed over a long period of time. On the basis of the results of X-ray photoelectron spectroscopy (XPS), transmission electron microscopy (TEM/EDX) and high-resolution X-ray fluorescence (HRXRF), in the case of using a silica or silica-titania support, eluted nickel components were confirmed to be nickel oxide present alone on the support. Since nickel oxide is a soluble compound in acid, in the case of using as a catalyst for carboxylic acid ester synthesis, it is presumed to be eluted by acidic substances exemplified by methacrylic acid or acrylic acid that are unique by-products of the reaction.

On the basis of analyses of the chemical state of nickel by high-resolution X-ray fluorescence (HRXRF), the nickel in the supported composite particle material according to the present embodiment is presumed to not contain a single compound in the form of nickel oxide alone, but rather form composite oxides containing nickel such oxidized compounds of nickel formed as a result of bonding between nickel oxide and constituent component elements of the support, or a solid solution or mixture thereof.

High-resolution X-ray fluorescence (HRXRF) has extremely high energy resolution and is able to analyze chemical state from the energy levels (chemical shifts) and shapes of the resulting spectrum. In the $K\alpha$ spectra of 3d transition metal elements in particular, changes appear in chemical shift and shape due to changes in valence or electronic state, thereby making it possible analyze the chemical state in detail. In the supported composite particle material according to the present embodiment, changes appear in the Ni $K\alpha$ spectrum, and a chemical state was confirmed for nickel that differs from that of a single compound in the form of nickel oxide.

For example, nickel aluminate, which is formed from nickel oxide and alumina, is a compound that is insoluble in acid. As a result of forming such a nickel compound on a support, elution of nickel components is presumed to be greatly improved.

In a preferable elementary composition of the support comprised of an aluminum-containing silica-based composition containing silica and alumina, the amount of aluminum is from 1 to 30 mol %, preferably from 5 to 30 mol % and more preferably from 5 to 25 mol % based on the total molar amount of silicon and aluminum. If the amount of aluminum is within the above ranges, acid resistance and mechanical strength tend to be satisfactory.

In addition, the support in the supported composite particle material according to the present embodiment preferably further contains an oxide of at least one of basic metals selected from the group consisting of alkaline metals, alkaline earth metals and rare earth metals, in addition to silica and alumina, from the viewpoint of further improving mechanical strength and chemical stability. Examples of alkaline metals of the basic metal components may include Li, Na, K, Rb and Cs, examples of alkaline earth metals may include Be, Mg, Ca, Sr and Ba, while examples of rare earth metals may include La, Ce and Pr.

In the elementary composition of the support containing silica, alumina and at least one of basic metals selected from the group consisting of alkaline metals, alkaline earth metals and rare earth metals, the amount of aluminum is from 1 to 30 mol %, preferably from 5 to 30 mol % and more preferably from 5 to 25 mol % based on the total molar amount of silicon and aluminum. In addition, the compositional ratio of basic metal oxide to alumina, in terms of the atomic ratio of (alkaline metal+½×alkaline earth metal+⅓× rare earth metal)/Al, is preferably within a range of from 0.5 to 10, more preferably within a range of from 0.5 to 5.0 and even more preferably within a range of from 0.5 to 2.0. If the elementary composition of silica, alumina and basic metal oxide is within the above ranges, the silicon, aluminum and basic metal oxide form a specific stable bonding structure, and as a result thereof, the mechanical strength and water resistance of the support tend to be satisfactory.

The following provides an explanation of a preferable method for preparing a support having a composition as described above.

There are no particular limitations on the method for preparing a support comprised of an aluminum-containing silica-based composition containing silica and alumina, and an aluminum-containing silica-based composition obtained according to any of (1) to (5) below can be prepared by firing under conditions to be described later.

(1) Use of a commercially available silica-alumina compound solution
(2) Reacting a silica sol with an aluminum compound solution
(3) Reacting a silica sol with an aluminum compound insoluble in water
(4) Reacting a silica gel with an aqueous solution of a water-soluble aluminum compound
(5) Reacting a silica gel and an aluminum compound in a solid phase reaction The following provides a detailed explanation of the support preparation methods referred to in (2) to (5) above.

In the methods of (2) to (5) above, a silica sol or silica gel is used for the silica source. The silica gel is that having non-crosslinked Si sites that react with Al, and there are no particular restrictions on the length of the Si—O chain. Although water-soluble compounds such as sodium aluminate, aluminum chloride hexahydrate, aluminum perchlorate hexahydrate, aluminum sulfate, aluminum nitrate nonahydrate or aluminum diacetate are preferable for the aluminum compound, compounds that are insoluble in water, such as aluminum hydroxide or aluminum oxide, can also be used provided they are compounds that react with non-crosslinked Si in the silica sol and silica gel.

In the case of the methods of (2) and (3) that use a silica sol as a starting material, after obtaining a mixed sol containing silica sol and an aluminum compound by mixing the silica sol and an aluminum compound, the mixed sol is subjected to a hydrothermal reaction at 20 to 100° C. for 1 to 48 hours and dried to obtain a gel followed by firing under temperature, time and atmospheric conditions to be described later. Alternatively, an alkaline aqueous solution is added to the above-mentioned mixed sol followed by co-precipitating silica and an aluminum compound, drying and firing under conditions to be described later. In addition, a support comprised of an aluminum-containing silica-based composition having a desired particle diameter can be obtained by either pulverizing the above-mentioned mixed sol directly using a spray dryer or by a step in which the mixed sol is dried following by granulating the gel.

In the case of the method of (3) in particular, although a silica sol is reacted with an aluminum compound insoluble in water, at this time the aluminum compound can be pulverized in advance to a prescribed particle diameter or can be preliminarily coarsely pulverized. After mixing and reacting the silica sol and the water-insoluble aluminum compound and drying, the mixture is further fired under conditions to be described later. The fired silica-alumina compound may also be pulverized to a prescribed particle diameter without pre-pulverizing the aluminum compound.

In the case of the method of (4) using a silica gel for the starting material, an aqueous solution of a water-soluble aluminum compound is reacted with the silica gel, and the silica gel may be pulverized to a prescribed particle diameter in advance, or may be preliminarily coarsely pulverized. After mixing and reacting the silica gel with the water-soluble aluminum compound at 20 to 100° C. for 1 to 48 hours, the mixture is dried and further fired for 1 to 48 hours under conditions to be described later. The fired silica-alumina compound may also be pulverized to a prescribed particle diameter without preliminarily pulverizing the silica gel.

The method of (5), which similarly uses a silica gel for the starting material, involves the preparation of an aluminum-containing silica composition by reacting the silica gel with an aluminum compound in a solid phase reaction. The Al is reacted in a solid phase state with non-crosslinked Si. The silica gel and the aluminum compound may be pulverized to a prescribed particle diameter in advance. In addition, they may also be preliminarily coarsely pulverized. Pulverization may be carried out for each substance alone or may be carried out after mixing both substances. Firing is carried out under temperature, time and atmospheric conditions to be described later. After the reaction, the resulting aluminum-containing silica composition can also be used after pulverizing to a prescribed particle diameter following the reaction without preliminarily pulverizing the silica gel and aluminum compound.

In a method for preparing a support containing silica, alumina and an oxide of at least one of basic metals selected from the group consisting of alkaline metals, alkaline earth metals and rare earth metals, the support can be prepared by drying a slurry obtained by mixing an alkaline metal oxide, alkaline earth metal oxide and/or rare earth metal oxide into silica and aluminum components and then firing under conditions to be described later in accordance with the above-mentioned method for preparing a support comprised of an aluminum-containing silica-based composition containing silica and alumina.

A typical commercially available compound can be used as a raw material of the alkaline metal, alkaline earth metal or rare earth metal in the same manner as the aluminum raw materials. The raw material is preferably a water-soluble compound and more preferably a hydroxide, carbonate, nitrate or acetate.

In another preparation method that can be used, a basic metal component selected from the group consisting of alkaline metals, alkaline earth metals and rare earth metals is adsorbed onto a support comprised of an aluminum-containing silica-based composition. For example, a method using an immersion method in which a support is added to a liquid in which is dissolved a basic metal compound followed by drying treatment, or a method using an impregnation method in which a basic metal compound equivalent to pore volume is worked into a support followed by drying treatment, can be applied. However, a method in which the basic metal component is adsorbed later requires caution in that liquid drying treatment must be carried out under mild conditions after having highly dispersed the basic metal component in the support.

In addition, inorganic substances or organic substances can be added to the mixed slurry of each of the raw materials described above in order to control slurry properties and finely adjust the pore structure or other characteristics of the product or the properties of the resulting support.

Specific examples of inorganic substances used may include inorganic acids such as nitric acid, hydrochloric acid or sulfuric acid, salts of metals such as alkaline metals such as Li, Na, K, Rb or Cs or alkaline earth metals such as Mg, Ca, Sr or Ba, water-soluble compounds such as ammonia or ammonium nitrate, and clay minerals that form a suspension by being dispersed in water. In addition, specific examples of organic substances may include polymers such as polyethylene glycol, methyl cellulose, polyvinyl alcohol, polyacrylic acid, polyacrylamide or the like.

Although there are various effects of adding inorganic substances or organic substances, the main effects include the formation of a spherical support and controlling pore diameter and pore volume. More specifically, the liquid properties of the mixed slurry are an important factor in obtaining a spherical support. Adjusting viscosity and solid content using an inorganic substance or inorganic substance makes it possible to alter the liquid properties to facilitate the obtaining of a spherical support. In addition, pore diameter and pore volume can be controlled by selecting the optimum organic compound that remains inside the support at the molding stage after which residual substances are able to be removed during firing after molding and by washing.

The support can be produced by spray-drying the mixed slurry of each raw material and additive described above. A known spraying device of, for example, a rotating disk type, two-fluid nozzle type or pressurized nozzle type can be used as the method for converting the mixed slurry into liquid droplets.

The liquid to be sprayed is required to be used in a well-mixed state. If the liquid is not properly mixed, it affects the performance of the support, such as decreased durability caused by uneven distribution of components. When formulating the raw materials in particular, increases in slurry viscosity or partial gelling (colloidal condensation) may occur, resulting in the risk of the formation of non-uniform particles. Consequently, in addition to taking into consideration gradually mixing the raw materials while stirring, for example, controlling a pH to a semi-stable region of the silica sol such as around pH 2 may be preferable by using a method such as adding acid or alkali.

The liquid to be sprayed is also required to have a certain degree of viscosity and solid content. If viscosity and solid content are excessively low, the porous body obtained by spray-drying may not form a perfect sphere and instead may form numerous indentations therein. In addition, if viscosity and solid content are excessively high, in addition to having a detrimental effect on the dispersibility of porous bodies, stable droplets are unable to be formed depending on the properties thereof. Consequently, the viscosity is preferably within a range of from 5 to 10,000 cps provided the liquid is able to be sprayed, and in terms of shape, higher viscosities tend to be preferable provided the liquid is able to be sprayed, while in consideration of the balance with ease of manipulation, the viscosity is selected to be within a range of from 10 to 1,000 cps. In addition, a solid content within a range of from 10 to 50% by mass is preferable in terms of shape and particle diameter. Furthermore, as a general reference for spray-drying conditions, the hot air temperature at the entrance to the drying tower of the spray dryer is preferably within a range of from 200 to 280° C., and the drying tower outlet temperature is preferably within a range of from 110 to 140° C.

The support firing temperature is typically selected to be within a range of from 200 to 800° C. If the support is fired at a temperature above 800° C., specific surface area tends to decrease considerably, thereby making this undesirable. In addition, although there are no particular limitations on the firing atmosphere, firing is typically carried out in air or nitrogen. In addition, although the firing time can be determined according to the specific surface area after firing, it is generally from 1 to 48 hours. Since firing conditions cause changes in the porosity and other properties of the support, it is necessary to select suitable temperature conditions and heating conditions. If the firing temperature is too low, it tends to be difficult to maintain durability as a composite oxide, while if the firing temperature is too high, there is the risk of causing a decrease in pore volume. In addition, heating conditions are preferably such that the temperature rises gradually by using a heating program and the like. In the case of firing under extremely high temperature conditions, gasification and combustion of inorganic substances and organic substances becomes violent, thereby exposing the support to a high-temperature state beyond that which has been set and causing the support to be pulverized.

From the viewpoints of ease of supporting composite particles, reaction activity in the case of using as a catalyst, resistance to separation and reaction activity, the specific surface area of the support is preferably 10 m$^2$/g or more, more preferably 20 m$^2$/g or more, and even more preferably 50 m$^2$/g or more as measured by BET nitrogen adsorption. Although there are no particular limitations on specific surface area from the viewpoint of activity, from the viewpoints of mechanical strength and durability, the specific surface area is preferably 700 m$^2$/g or less, more preferably 350 m$^2$/g or less and even more preferably 300 m$^2$/g or less.

The pore structure of the support is an extremely important property in terms of long-term stability, including supporting characteristics of metal components other than strength, as well as reaction characteristics. Pore diameter is a physical property value required to demonstrate these characteristics. If pore diameter is smaller than 3 nm, although the separation properties of the supported metal tend to be satisfactory, in the case of using as a catalyst in a liquid phase reaction and the like, pore diameter is preferably 3 nm or more from the viewpoint of not making the intrapore diffusion resistance excessively great so that the diffusion process of the reaction substrate is not rate-limiting as well as maintaining reaction activity at a high level. On the other hand, the pore diameter is preferably 50 nm or less from the viewpoints of resistance to cracking of the supported material and resistance to separation of the supported metal. Thus, the pore diameter of the support is preferably from 3 to 50 nm, and more preferably from 3 to 30 nm. Pore volume is required for the presence of pores capable of supporting compounded nanoparticles. However, if pore volume is excessively large, a tendency is observed for strength to suddenly decrease. Thus, from the viewpoints of strength and supporting characteristics, pore volume is preferably within a range of from 0.1 to 1.0 mL/g and more preferably within a range of from 0.1 to 0.5 mL/g. The support of the present embodiment preferably satisfies the above ranges for both pore diameter and pore volume.

The shape of the support is selected according to the reaction form, selecting a hollow cylindrical support or honeycomb structure resulting in little pressure loss in the case of a fixed bed reaction, while under conditions of a liquid phase slurry suspension, a spherical shape is generally selected after selecting the optimum particle diameter in consideration of reactivity and the separation method. For example, in the case of employing a generally simple catalyst separation process based on precipitation separation, a particle diameter of from 10 to 20 μm is preferably selected, that of from 20 to 150 μm is more preferably selected and that of from 30 to 150 μm is even more preferably selected based on the balance with reaction characteristics. In the case of a cross filter reaction, small particles of 0.1 to 20 μm or less are preferable since they yield higher reactivity. The supported composite particle material can thus be used as a catalyst for chemical synthesis by changing the type and form of the support according to the purpose of use.

Although there are no particular limitations on the loading of oxidized nickel on the support, the loading of oxidized nickel is generally from 0.01 to 20% by mass, preferably from 0.1 to 10% by mass, more preferably from 0.2 to 5% by mass and even more preferably 0.5 to 2% by mass as nickel based on the weight of the support. The loading of X supported onto the support is generally from 0.01 to 10% by mass, preferably from 0.1 to 5% by mass, more preferably from 0.2 to 2% by mass, even more preferably from 0.3 to 1.5% by mass and particularly preferably from 0.5 to 1.0% by mass as metal based on the weight of the support.

Moreover, in the present embodiment, a preferable range exists for the atomic ratio between nickel and the above-mentioned constituent elements of the support. In the case of using the support comprised of an aluminum-containing silica-based composition containing silica and alumina in the present embodiment, the compositional ratio of nickel and alumina in a catalyst in terms of the atomic ration of Ni/Al is preferably from 0.01 to 1.0, more preferably from 0.02 to 0.8 and even more preferably from 0.04 to 0.6. In addition, in the case of using a support containing silica, alumina and an oxide of at least one of basic metals selected from the group consisting of alkaline metals, alkaline earth metals and rare earth metals, the atomic ratio of nickel and alumina in the supported material in terms of the atomic ratio of Ni/Al is preferably from 0.01 to 1.0, more preferably from 0.02 to 0.8 and even more preferably from 0.04 to 0.6, and the compositional ratio of nickel and alkaline metal component in terms of the atomic ratio of Ni/(alkaline metal+alkaline earth metal+ rare earth metal) is preferably from 0.01 to 1.2, more preferably from 0.02 to 1.0 and even more preferably from 0.04 to 0.6.

If the atomic ratios of nickel to support constituent elements in the form of aluminum and basic metal oxide are within the above ranges, the effects of improving nickel elution and structural changes in supported particle materials tend to increase. This is thought to be because the nickel, aluminum and basic metal oxide form a specific composite oxide within the above ranges, thereby forming a stable bonding structure.

The supported composite particle material according to the present embodiment can also contain a third constituent element in addition to the active components in the form of oxidized nickel and X. Examples of third constituent elements that can be contained may include titanium, vanadium, chromium, manganese, lead, cobalt, zinc, gallium, zirconium, niobium, molybdenum, rhodium, cadmium, indium, tin, antimony, tellurium, hafnium, tantalum, tungsten, rhenium, osmium, iridium, mercury, thallium, lead, bismuth, aluminum, boron, silicon and phosphorous. The content of these third constituent elements is preferably from 0.01 to 20% by mass and more preferably from 0.05 to 10% by mass in the supported material. In addition, at least one of metal component selected from the group consisting of alkaline metals, alkaline earth metals and rare earth metals may also be contained in the supported composite particle material. The content of alkaline metal, alkaline earth metal or rare earth metal is preferably selected to be within a range of 15% by mass or less in the supported material.

Furthermore, these third constituent elements or alkaline metal, alkaline earth metal or rare earth metal may be contained in the supported composite particle material during production or reaction of the supported composite particle material, or a method may be used in which they are contained in the support in advance.

The specific surface area of the supported composite particle material according to the present embodiment is preferably within a range of from 20 to 350 m$^2$/g, more preferably from 50 to 300 m$^2$/g and even more preferably from 100 to 250 m$^2$/g as measured by BET nitrogen adsorption from the viewpoints of reaction activity and resistance to separation of active components.

The pore structure of the supported composite particle material is an extremely important property in terms of long-term stability, including supporting characteristics and separation of metal components, as well as reaction characteristics, and pore diameter is a physical property value required to demonstrate these characteristics. If pore diameter is smaller than 3 nm, although the separation properties of the supported metal component tend to be satisfactory, in the case of using as a catalyst in a liquid phase reaction and the like, pore diameter is preferably 3 nm or more from the viewpoint of not making the intrapore diffusion resistance excessively great so that the diffusion process of the reaction substrate is not rate-limiting as well as maintaining reaction activity at a high level. On the other hand, the pore diameter is preferably 50 nm or less from the viewpoints of resistance to cracking of the supported material and resistance to separation of the supported composite particles. Thus, the pore diameter of the supported composite particle material is preferably from 3 to 50 nm, more preferably from 3 to 30 nm and even more preferably from 3 to 10 nm. From the viewpoints of supporting characteristics and reaction characteristics, pore volume is preferably within a range of from 0.1 to 1.0 mL/g, more preferably within a range of from 0.1 to 0.5 mL/g and even more preferably within a range of from 0.1 to 0.3 mL/g. The supported composite particle material according to the present embodiment preferably satisfies the above ranges for both pore diameter and pore volume.

[Process for Producing Supported Composite Particle Material]

There are no particular limitations on the method used to prepare the supported composite particle material according to the present embodiment provided a supported material as described above is obtained. The following provides an explanation of a typical process for preparing the supported composite particle material according to the present embodiment.

In a first step, an aqueous slurry containing a support supported with an oxide of at least one of basic metals selected from the group consisting of alkaline metals, alkaline earth metals and rare earth metals is mixed with an acidic aqueous solution of a soluble metal salt containing nickel and X (wherein X represents at least one of elements selected from the group consisting of nickel, palladium, platinum, ruthenium, gold, silver and copper). The temperature of the mixture of both liquids is adjusted so that the temperature thereof is 60° C. and above. A precursor of a supported composite particle material in which nickel and the X component have precipitated is formed on the support in the mixture.

Next, in a second step, the precursor obtained in the first step is rinsed with water and dried as necessary followed by subjecting to heat treatment to obtain the supported composite particle material according to the present embodiment.

According to this process, a supported composite particle material can be obtained that has a supported layer in which the composite particles are localized but does not contain composite particles in a region that includes the center of the support.

Prior to the first step, the support supported with an oxide of at least one of basic metals selected from the group consisting of alkaline metals, alkaline earth metals and rare earth metals is preferably aged in water. Aging the support in advance allows the obtaining of a layer having a sharp distribution of composite particles. Based on the results of measuring pore distribution by nitrogen adsorption, the effect produced by aging the support is presumed to be the result of a more uniform and sharper pore structure due to the occurrence of realignment of the support pore structure. Although support aging can be carried out at room temperature, due to the slow rate of changes in the pore structure thereof, a temperature higher than room temperature is preferably selected within a range of from 60 to 150° C. In the case of aging at normal pressure, a temperature within a range of from 60 to 100° C. is preferable. In addition, although the duration of aging treatment varies according to the temperature conditions, it is preferably from 1 minute to 5 hours, more preferably from 1 to 60 minutes and even more preferably from 1 to 30 minutes at a temperature of 90° C., for example. In the procedure of the first step, although the support can be used after initially drying and then firing after it has been aged, a slurry in which the support is dispersed in water is preferably contacted with the acidic aqueous solution of a soluble metal salt containing nickel and X followed by insoluble fixation of the nickel and X on the support.

Examples of soluble metal salts containing nickel used to prepare a catalyst may include nickel nitrate, nickel acetate, nickel chloride or the like. In addition, examples of soluble metal salts containing X may include palladium chloride, palladium acetate or the like in the case of selecting palladium for X, ruthenium chloride, ruthenium nitrate or the like in the case of selecting ruthenium for X, chloroauric acid, sodium tetrachloroaurate, potassium dicyanoaurate, gold diethylamine trichloride, gold cyanide or the like in the case of selecting gold for X, and silver chloride, silver nitrate or the like in the case of selecting silver for X.

The respective concentrations of aqueous solutions containing nickel and X are generally within a range of from 0.0001 to 1.0 mol/L, preferably from 0.001 to 0.5 mol/L and more preferably from 0.005 to 0.2 mol/L. The ratio of nickel and X in the aqueous solutions in terms of the atomic ratio of Ni/X is preferably within a range of from 0.1 to 10, preferably from 0.2 to 5.0 and more preferably from 0.5 to 3.0.

The temperature during contact between the nickel and acidic aqueous solution of a soluble metal salt containing nickel and X is one important factor for controlling the distribution of composite particles, and although varying according to the amount of oxide of at least one of basic metals selected from the group consisting of alkaline metals, alkaline earth metals and rare earth metals supported in advance onto the support, if the temperature is excessively low, the reaction slows and the distribution of composite particles tends to widen. In the production process according to the present embodiment, the temperature during contact with the acidic aqueous solution of a soluble metal salt containing nickel and X, from the viewpoint of obtaining a supported layer in which the composite particles are more sharply localized, is a temperature at which the supported composite particle material is obtained at a high reaction rate, and is preferably 60° C. or higher, more preferably 70° C. or higher, even more preferably 80° C. or higher and particularly preferably 90° C. or higher. Since the acidic aqueous solution and aqueous slurry are mixed so that the temperature of the mixed liquid thereof is 60° C. or higher, the aqueous slurry may be heated to a degree such that the mixed liquid exceeds 60° C. even after the acidic aqueous solution is added, or conversely only the acidic aqueous solution may be heated. Both the acidic aqueous solution and the aqueous slurry may naturally also be heated to 60° C. or higher.

Although the reaction can be carried out under an applied pressure at a temperature equal to or higher than the boiling point of the solvent, based on the ease of the procedure, it is generally preferably carried out at a temperature equal to or lower than the solvent boiling point. There are no particular limitations on the duration of fixation of the nickel and X components, and although varying according to conditions such as the type of support, the loading of nickel and X and the ratio thereof, the duration is generally within a range of from 1 minute to 5 hours, preferably from 5 minutes to 3 hours and more preferably from 5 minutes to 1 hour.

The production process of the supported composite particle material according to the present embodiment is based on the principle of insoluble fixation of the nickel and X components by carrying out a chemical reaction between an oxide of at least one of basic metals selected from the group consisting of alkaline metals, alkaline earth metals and rare earth metals supported in advance on the support, and a soluble metal salt containing nickel and X. These components are preferably fixed simultaneously from a mixed solution containing both components in order to ensure more adequate compounding of the nickel and X.

In addition, in the production process according to the present embodiment, the aqueous slurry containing a support supported with an oxide of at least one of basic metals selected from the group consisting of alkaline metals, alkaline earth metals and rare earth metals preferably contains a salt of at least one of basic metals selected from the group consisting of alkaline metals, alkaline earth metals and rare earth metals.

As a result, the formation of metal black of X is inhibited, compounding of nickel and X is promoted, and the distribution of composite particles can be controlled more precisely. Such effects are presumed to be caused by controlling the rate of the chemical reaction between the basic metal oxide supported in advance on the support and the soluble metal salt containing nickel and X as a result of adding to the aqueous solution a salt of at least one of metals selected from the group consisting of alkaline metals, alkaline earth metals and rare earth metals.

Examples of salts of at least one of basic metals selected from the group consisting of alkaline metals, alkaline earth metals and rare earth metals that can be used may include one or more types selected from water-soluble salts of these metals such as organic acid salts, nitrates, chlorides or the like.

The amount of the salt of at least one of basic metals selected from the group consisting of alkaline metals, alkaline earth metals and rare earth metals as described above varies according to the amounts and ratio of the nickel and X components, and is determined according to the amount of basic metal oxide supported in advance onto the support. Generally, the amount of the above salt is from 0.001 to 2 times moles and preferably from 0.005 to 1 times moles based on the amount of nickel and X components in the aqueous solution.

In addition, the aqueous slurry containing a support supported with an oxide of at least one of basic metals selected from the group consisting of alkaline metals, alkaline earth metals and rare earth metals preferably contains a soluble aluminum salt. Examples of soluble aluminum salts that can be used may include aluminum chloride and aluminum nitrate.

The addition of a soluble aluminum salt to the aqueous slurry allows the formation of an outer layer substantially free of composite particles on the outside of the supported layer in which composite particles are localized. This is also based on the principle of insoluble fixation as previously described. Aluminum chloride or aluminum nitrate and the like is used for the soluble aluminum salt, aluminum is reacted on the outer surface of the support by a chemical reaction with the basic metal oxide supported in advance onto the support, the nickel and X are consumed thereby, and the outer layer is fixed by a reaction between the basic metal oxide inside and the nickel and X.

The amount of aluminum component varies according to how many μm the thickness of the layer not supported with nickel or X component is set to, and is determined according to the amount of basic metal oxide supported in advance onto the support. Generally, the amount of aluminum component is from 0.001 to 2 times moles and preferably from 0.005 to 1 times moles based on the amount of basic metal oxide supported in advance onto the support.

Although there are many aspects of the details of the mechanism by which the nickel and X components are distributed that are unclear, it is presumed that the balance with the rate at which the components are insolubilized by a chemical reaction was effectively attained under the conditions of the present embodiment, thereby making it possible to fix the composite particles in a narrow region near the surface of the support.

In addition, in the case of forming the outer layer substantially free of composite particles on the outer surface of the support, since aluminum and a basic metal component near the outer surface of the support are allowed to react resulting in consumption of basic metal components capable of reacting with nickel and X components near the outer surface of the support, and when nickel and X are subsequently supported, the reactive basic metal components near the outer surface of the support are already consumed, the nickel and X are presumed to be fixed as a result of reacting with a basic metal compound inside the support.

The following provides an explanation of the second step.

The precursor of the supported composite particle material is rinsed with water and dried as necessary prior to the heat treatment of the second step. The temperature at which the precursor is heated is generally from 40 to 900° C., preferably from 80 to 800° C., more preferably from 200 to 700° C. and even more preferably from 300 to 600° C.

Heat treatment is carried out in an atmosphere such as air (or atmospheric air), an oxidizing atmosphere (such as oxygen, ozone, nitrogen oxides, carbon dioxide, hydrogen peroxide, hypochlorous acid or inorganic or organic peroxides), or an inert gas atmosphere (such as helium, argon or nitrogen). The heating time is suitably selected according to the heating temperature and amount of precursor. In addition, heat treatment can be carried out at normal pressure, under applied pressure or under reduced pressure.

Following the second step as described above, reduction treatment can be carried out in a reducing atmosphere (such as hydrogen, hydrazine, formalin or formic acid) as necessary. In this case, a treatment method is selected that prevents the oxidized nickel from being completely reduced to a metallic state. The temperature and duration of reducing treatment are suitably determined according to the type of reducing agent, type of X and amount of catalyst.

Moreover, oxidizing treatment can be carried out following the above-mentioned heat treatment and reducing treatment in air (or atmospheric air) or an oxidizing atmosphere (such as oxygen, ozone, nitrogen oxides, carbon dioxide, hydrogen peroxide, hypochlorous acid or inorganic or organic peroxides) as necessary. The temperature and duration in this case is suitably determined according to the type of oxidizing agent, type of X and amount of catalyst.

A third constituent element other than nickel and X can be added during production of the supported material or under reaction conditions. The alkaline metal, alkaline earth metal or rare earth metal can also be added during catalyst preparation or to the reaction system. In addition, the raw materials of the third constituent element, alkaline metal, alkaline earth metal and rare earth metal are selected from salts of organic acids, salts of inorganic acids, hydroxides and the like.

As has been described above, according to the supported composite particle material production process according to the present embodiment, the supported composite particle material can be obtained having the supported layer in which composite particles are localized comprised of oxidized nickel and X in specific shallow region near the outer surface of the support, and as necessary, having a layer substantially free of the composite particles on the outer surface of the support.

[Process for Producing Compounds Using the Supported Composite Particle Material as a Catalyst for Chemical Synthesis]

The supported composite particle material according to the present embodiment can be widely used as a catalyst for chemical synthesis. For example, it can be used as a catalyst or photocatalyst of reactions such as reactions for forming carboxylic acid esters from aldehydes and alcohols, reactions for forming carboxylic acid esters from alcohols, alkane oxidation reactions, alcohol oxidation reactions, aldehyde oxidation reactions, olefin oxidation reactions, olefin epoxidation reactions, olefin oxidative addition reactions, amine oxidation reactions, olefin hydrogenation reactions, $\alpha,\beta$-unsaturated ketone hydrogenation reactions, reactions for forming hydrogen peroxide from hydrogen and oxygen, carbon monoxide oxidation reactions and NOx reduction.

The supported composite particle material according to the present embodiment demonstrates superior effects particularly in the case of using as a catalyst of an oxidation reaction. In addition to the aldehydes and alcohols used in the reaction for forming carboxylic acid ester as indicated in the examples, other examples of reaction substrates used in the present embodiment may include various reaction substrates such as alkanes, olefins, alcohols, ketones, aldehydes, ethers, aromatic compounds, phenols, sulfur compounds, phosphorous compounds, oxygen-containing nitrogen compounds, amines, carbon monoxide and water. These reaction substrates can be used alone, or two or more types can be used as a mixture. Various industrially useful oxygen-containing compounds, oxidative addition products, oxidative dehydrogenation products and other oxidation products are obtained from these reaction substrates.

Specific examples of reaction substrates in the form of alkanes may include aliphatic alkanes such as methane, ethane, propane, n-butane, isobutane, n-pentane, n-hexane, 2-methylpentane or 3-methylpentane, and alicyclic alkanes such as cyclopentane, cyclohexane, cycloheptane or cyclooctane.

Examples of olefins may include aliphatic olefins such as ethylene, propylene, butene, pentene, hexene, heptene, octene, decene, 3-methyl-1-butene, 2,3-dimethyl-1-butene or allyl chloride, alicyclic olefins such as cyclopentene, cyclohexene, cycloheptene, cyclooctene or cyclodecene, and aromatic substituted olefins such as styrene or $\alpha$-methylstyrene.

Examples of alcohols may include saturated and unsaturated aliphatic alcohols such as methanol, ethanol, n-propanol, isopropanol, n-butanol, s-butanol, t-butanol, n-pentanol, n-hexanol, n-heptanol, allyl alcohol or crotyl alcohol, saturated and unsaturated alicyclic alcohols such as cyclopentanol, cyclohexanol, cycloheptanol, methylcyclohexanol or cyclohexen-1-ol, aliphatic and alicyclic polyvalent alcohols such as ethylene glycol, propylene glycol, trimethylene glycol, 1,3-butanediol, 1,2-cyclohexanediol or 1,4-cyclohexanediol, and aromatic alcohols such as benzyl alcohol, salicyl alcohol or benzhydrol.

Examples of aldehydes may include aliphatic saturated aldehydes such as formaldehyde, acetoaldehyde, propionaldehyde, isobutylaldehyde or glyoxal, aliphatic $\alpha,\beta$-unsaturated aldehydes such as acrolein, methacrolein or crotonaldehyde, aromatic aldehydes such as benzaldehyde, tolylaldehyde, benzylaldehyde or phthalaldehyde, and derivatives of these aldehydes.

Examples of ketones may include aliphatic ketones such as acetone, methyl ethyl ketone, diethyl ketone, dipropyl ketone or methyl propyl ketone, alicyclic ketones such as cyclopentanone, cyclohexanone, cyclooctanone, 2-methylcyclohexanone or 2-ethylcyclohexanone, and aromatic ketones such as acetophenone, propiophenone and benzophenone.

Examples of aromatic compounds may include benzene, toluene, xylene, naphthalene, anthracene and derivatives thereof substituted with, for example, alkyl groups, aryl groups, halogens or sulfone groups.

Examples of phenols may include phenol, cresol, xylenol, naphthol, anthrol (hydroxyanthracene) and derivatives thereof (such as those in which aromatic hydrogen atoms are substituted with alkyl groups, aryl groups, halogen atoms or sulfone groups).

Examples of sulfur compounds may include mercaptans such as methyl mercaptan, ethyl mercaptan, propyl mercaptan, benzyl mercaptan or thiophenol.

Examples of amines may include aliphatic amines such as methylamine, ethylamine, propylamine, isopropylamine, butylamine, dimethylamine, diethylamine, dipropylamine, diisopropylamine, dibutylamine, trimethylamine, triethylamine, tripropylamine, tributylamine, allylamine or diallylamine, alicyclic amines such as cyclopentylamine, cyclohexylamine, cycloheptylamine or cyclooctylamine, and aromatic amines such as aniline, benzylamine or toluidine.

These reaction substrates can be used alone, or two or more types can be used as a mixture. In addition, these reaction substrates are not necessarily required to be purified, and may be in the form of mixtures with other organic compounds.

The following provides an explanation of an example of a process for producing carboxylic acid ester from aldehyde and alcohol in the presence of oxygen by an oxidative esterification reaction using the supported composite particle material according to the present embodiment as a catalyst.

Examples of the aldehyde used as a raw material may include $C_1$ to $C_{10}$ aliphatic aldehydes such as formaldehyde, acetoaldehyde, propionaldehyde, isobutylaldehyde, glyoxal or the like; $C_3$ to $C_{10}$ alicyclic $\alpha\cdot\beta$ unsaturated aldehydes such as acrolein, methacrolein, crotonaldehyde or the like; $C_6$ to $C_{20}$ aromatic aldehydes such as benzaldehyde, tolylaldehyde, benzylaldehyde, phthalaldehyde or the like; and derivatives of these aldehydes. These aldehyde can be used alone, or any two or more types can be used as a mixture.

Examples of alcohols may include $C_1$ to $C_{10}$ aliphatic saturated alcohols such as methanol, ethanol, isopropanol, butanol, 2-ethylhexanol, octanol or the like; $C_5$ to $C_{10}$ alicyclic alcohols such as cyclopentanol, cyclohexanol or the like; $C_2$ to $C_{10}$ diols such as ethylene glycol, propylene glycol, butanediol or the like; $C_3$ to $C_{10}$ aliphatic unsaturated alcohols such as allyl alcohol, methallyl alcohol or the like; $C_6$ to $C_{20}$ aromatic alcohols such as benzyl alcohol or the like; and hydroxyoxetanes such as 3-alkyl-3-hydroxymethyloxetane or the like. These alcohols can be used alone, or any two or more types can be used as a mixture.

There are no particular limitations on the weight ratio of aldehyde to alcohol, and although the reaction can be carried out over a wide range of molar ratios of aldehyde/alcohol of from 10 to 1/1,000 the reaction is generally carried out within the range of a molar ratio of from 1/2 to 1/50.

The amount of catalyst used can be varied considerably according to, for example, the types of reaction raw materials, composition and preparation method of the catalyst, reaction conditions and reaction form, and although there are no particular limitations thereon, in the case of reacting the catalyst in the form of a slurry, the amount of catalyst in terms of the solid content in the slurry is preferably within the range of from 1 to 50 wt/vol %, more preferably from 3 to 30 wt/vol % and even more preferably from 10 to 25 wt/vol %.

In the production of carboxylic acid ester, the reaction may be carried out either in batches or continuously using an arbitrary method such as a vapor phase reaction, liquid phase reaction or reflux reaction.

Although the reaction can be carried out in the absence of solvent, it can also be carried out using a solvent that is inert with respect to the reaction components such as hexane, decane, benzene, dioxane or the like.

A known form such as a fixed bed type, fluidized bed type or stirred tank type can be used for the reaction form. For example, when carrying out the reaction in a liquid phase, any type of reactor can be used, such as a bubble column reactor, draft tube type reactor, stirred tank reactor or the like.

The oxygen used to produce carboxylic acid ester can be molecular oxygen, namely can be in the form of oxygen gas itself or a mixed gas in which the oxygen gas has been diluted with a diluent that is inactive in the reaction such as nitrogen or carbon dioxide gas, and air is preferably used for the oxygen raw material from the viewpoints of ease of manipulation, economy and the like.

Although oxygen partial pressure varies according to the reaction raw materials such as the type of aldehyde or type of alcohol, the reaction conditions or the type of reactor and the like, the oxygen partial pressure at the reactor outlet is, for practical reasons, within the range equal to or lower than the lower limit of the explosive range, and is preferably controlled to, for example, from 20 to 80 kPa. Although reaction can be carried out at a reaction pressure extending over a wide pressure range from depressurization to pressurization, the reaction is normally carried out at a pressure within the range of from 0.05 to 2 MPa. In addition, it is preferable from the viewpoint of safety to set the total pressure so that the oxygen concentration of the reactor outflow gas does not exceed the explosive limit (for example, a concentration of 8%).

In the case of carrying out a carboxylic acid ester production reaction in a liquid phase, the pH of the reaction system is preferably maintained at from 6 to 9 by adding a compound of an alkaline metal or alkaline earth metal (such as an oxide, hydroxide, carbonate or carboxylate) to the reaction system. These alkaline metal or alkaline earth metal compounds can be used alone, or two or more types can be used in combination.

Although the reaction temperature during production of carboxylic acid ester is such that the reaction can be carried out at high temperatures above 200° C., the reaction temperature is preferably from 30 to 200° C., more preferably from 40 to 150° C. and even more preferably from 60 to 120° C. There are no particular limitations on the reaction time, and although not determined unconditionally since it varies according to the set conditions, it is generally from 1 to 20 hours.

EXAMPLES

Although the following provides a more detailed explanation of the present embodiment through examples and comparative examples thereof, the present embodiment is not limited thereto. A person with ordinary skill in the art can not only carry out the examples indicated below, but also make various changes thereto, and such changes are also included within the scope of the claims for patent.

Furthermore, in the examples and comparative examples, measurement of the distributions of nickel and X in the supported composite particle material, observation of the form of the support and supported composite particle material, measurement of mean particle diameter, determination of the loading of Ni and X and atomic ratio of Ni/(Ni+X), determination of the content of support constituent elements (Si, Al, basic metal), analysis of the crystal structure of composite particles, analysis of the chemical state of composite particle metal elements, analysis of the chemical state of nickel, morphological observation and elementary analysis of composite particles, measurement of the ultraviolet-visible spectra of composite particles and measurement of the physical properties of the support and supported composite particle material (specific surface area, pore diameter, pore volume) were carried out according to the methods described below.

[Measurement of Distributions of Nickel and X in Supported Composite Particle Material]

A sample obtained by embedding the resulting supported composite particle material in resin and polishing was measured at an acceleration voltage of 15 kV using the Shimadzu Model 1600 X-ray Microprobe (EPMA). Ni and X (Au) in the direction of depth from the outer surface were analyzed on the basis of electron reflected images and X-ray analysis (Ni— wavelength: 14.5829, analyzing crystal: RAP; X (Au)— wavelength: 5.8419, analyzing crystal: PET).

[Morphological Observation of Support and Supported Composite Particle Material]

The support and supported composite particle material were observed using the Hitachi X-650 Scanning Electron Microscopy System (SEM).

[Measurement of Mean Particle Diameter of Support and Supported Composite Particle Material]

Mean particle diameter (volume-based) was measured using the Beckman-Coulter Model LS230 Laser Diffraction/Scattering Particle Size Distribution Measuring System.

[Determination of Loading of Ni and X and Atomic Ratio of Ni/(Ni+X)]

The concentrations of Nickel and X in the supported composite particle material were quantified using the Thermo Fisher Scientific Model IRIS Intrepid III XDL ICP Emission Spectrometer (ICP-AES, MS).

Samples were prepared by weighing out a supported material into a Teflon decomposition vessel, adding nitric acid and hydrogen fluoride and heating and decomposing with the Milestone General Model ETHOS-TC Microwave Decomposition System, followed by evaporating to dryness over a heater, adding nitric acid and hydrochloric acid to the precipitated residue, heating under an applied pressure with a microwave decomposition system, and using a fixed amount of the resulting pure decomposition product as a test liquid.

The quantification method was carried out by quantifying with ICP-AES with an internal standard and then determining the contents of nickel and X in the catalyst by subtracting a simultaneously determined blank value followed by calculating the loading and atomic ratio.

[Determination of Contents of Support Constituent Elements (Si, Al, Basic Metal]

Samples were prepared by dissolving the support with aqua regia and dissolving with molten alkali salt. The content of basic metal and/or Mg was measured for the sample dissolved with aqua regia and the contents of Al and Si were measured for the sample dissolved with molten alkali salt using the Seiko Instruments Model JY-38P2 ICP Emission Spectrometer (ICP-AES) followed by calculation of the atomic ratios from the resulting metal contents.

[Analysis of Crystal Structure of Composite Particles]

Crystal structure was analyzed using the Rigaku Model Rint 2500 Power X-Ray Diffraction System (XRD) under conditions of a Cu tube for the X-ray source (40 kV, 200 mA), measuring range of 5 to 65 degrees (0.02 deg/step), measuring speed of 0.2 deg/min and slit widths (scattering, divergence, reception) of 1 deg, 1 deg and 0.15 mm.

The sample was prepared by uniformly spraying onto a non-reflective sample plate and fixing with neoprene rubber.

[Analysis of Chemical State of Composite Particle Metal Components]

The chemical state of composite particle metal components was analyzed using the Thermo Electron Model ESCALAB 250 X-Ray Photoelectron Spectroscopy System (XPS) under conditions of Al Kα at 15 kV×10 mA for the excitation source, analyzed surface area of about 1 mm (shape: oval), using a 0 to 1,100 eV survey scan and an Ni2p narrow scan for the uptake region.

The measurement samples were prepared by crushing the supported composite particle material with an agate mortar and pestle and placing on a special-purpose powder sample stage followed by XPS measurement.

[Analysis of Chemical State of Nickel]

Ni Kα spectra were measured with the Technos Model XFRA190 High-Resolution X-Ray Fluorescence Spectroscopy System (HRXRF), and each of the resulting parameters was compared with those of standard substances (nickel metal, nickel oxide) to predict the chemical state such as valence of nickel present in the supported material.

The measurement samples were used directly for measurement. The Kα spectrum of Ni was measured in the partial spectral mode. At that time, Ge (220) was used for the analyzing crystal, a slit having a vertical divergence angle of 1 degree was used for the slit, and the excitation voltage and current were set to 35 kV and 80 mA, respectively. Filter paper was then used for the absorber in the case of the reference sample, counting time was selected for each sample in the case of supported material samples, and measurements were carried out so that the peak intensity of the Kα spectra was 3,000 cps or less and 10,000 counts or more. Measurement was repeated five times for each sample, and metal samples were measured before and after each repeated measurement. After subjecting measured spectra to smoothing processing (S-G method, 7 points, 5 times), the peak locations, half-width values (FWHM) and asymmetry indices (AI) were calculated, and peak locations were treated as a chemical shift ($\Delta E$) from the measured value of the metal sample measured before and after measurement of each sample.

[Morphological Observation and Elementary Analysis of Composite Particles]

TEM bright field images, STEM dark field images and STEM-EDS compositional analyses (point analyses, mapping, line analyses) were measured using the JEOL Model 3100FEF transmission electron microscope/scanning transmission electron microscope (TEM/STEM) (acceleration voltage: 300 kV, with energy dispersive X-ray detector (EDX)).

The data analysis software contained Digital Micrograph™ Ver. 1.70.16 from Gatan for TEM image and STEM image analyses (length measurement, Fourier transform analysis), and the NORAN System SIX Ver. 2.0 from Thermo Fisher Scientific for EDS data analyses (mapping image processing, compositional quantification and calculation).

The measurement samples were prepared by crushing the supported composite particle material with a mortar and pestle followed by dispersing in ethanol. After subjecting to ultrasonic cleaning for about 1 minute, the powder was dropped onto a molybdenum microgrid and air-dried to obtain TEM/STEM observation samples.

[Measurement of Ultraviolet-Visible Spectra of Composite Particles]

UV and visible spectra were measured using the Jasco Model V-550 Ultraviolet-Visible Spectrophotometer (UV-Vis) (with integrating sphere unit and powder sample holder) at a measuring range of 800 to 200 nm and scanning speed of 400 nm/min.

The measurement samples were prepared by crushing the supported composite particle material with an agate mortar and pestle and placing in the powder sample holder for measurement of UV-Vis spectra.

[Measurement of Physical Properties of Support and Supported Composite Particle Material Specific Surface Area, Pore Diameter, Pore Volume]

Physical properties were measured with the Yuasa Ionics 3 MP AutoSorb System using nitrogen gas for the adsorbing gas (nitrogen adsorption method). The BET method was used for specific surface area, the BJH method for pore diameter and pore distribution, and the amount of adsorption at maximum $P/P_0$ was used for pore volume.

Support Production Reference Example

An aqueous solution in which 3.75 kg of aluminum nitrate nonahydrate, 2.56 kg of magnesium nitrate and 540 g of 60% nitric acid were dissolved in 5.0 L of pure water was gradually dropped into 20.0 kg of a silica sol solution having a colloidal particle diameter of 10 to 20 nm while stirring and holding at 15° C. (Nissan Chemical Industries, Snowdex N-30, $SiO_2$ content: 30% by mass) to obtain a mixed slurry of silica sol, aluminum nitrate and magnesium nitrate. Subsequently, the mixed slurry was aged by holding at 50° C. for 24 hours. After cooling to room temperature, the mixed slurry was spray-dried with a spray dryer set to an outlet temperature of 130° C. to obtain a solid.

Next, the resulting solid was filled to a thickness of about 1 cm into a stainless steel container having an open top followed by heating an electric furnace from room temperature to 300° C. over the course of 2 hours and holding at that temperature for 3 hours. Moreover, after heating to 600° C. over the course of 2 hours and holding at that temperature for 3 hours, the solid was cooled to obtain a support. The resulting support contained 83.3 mol %, 8.3 mol % and 8.3 mol % of silicon, aluminum and magnesium, respectively, based on the total molar amount of silicon, aluminum and magnesium. The specific surface area as determined by nitrogen adsorption was 149 $m^2/g$, the pore volume was 0.27 mL/g and the mean pore diameter was 8 nm. The mean particle diameter of the support was 60 μm based on the results of measurement of laser diffraction/scattering particle size distribution. In addition, the form of the support was determined to be nearly spherical based on observations using a scanning electron microscope (SEM).

Example 1

300 g of the support obtained in the Support Production Reference Example were dispersed in 1.0 L of water heated to 90° C. followed by stirring for 15 minutes at 90° C. Next, an aqueous solution containing 16.35 g of nickel nitrate hexahydrate and 12 mL of a 1.3 mol/L aqueous solution of chloroauric acid was prepared followed by heating to 90° C., adding the above-mentioned support slurry and continuing to stir for 30 minutes at 90° C. to insolubly fix the nickel and gold component on the support.

Next, after removing the supernatant by allowing to stand undisturbed and washing several times with distilled water, the washed supernatant was filtered. After drying for 10 hours at 105° C. with a dryer, the product was fired for 5 hours at 450° C. in air in a muffle furnace to obtain a supported composite particle material (NiOAu/SiO$_2$—Al$_2$O$_3$—MgO) supported with 1.05% by mass of nickel and 0.91% by mass of gold. The atomic ratio of Ni/(Ni+Au) of the supported material thus obtained was 0.80.

A sample obtained by embedding the resulting supported composite particle material in resin and polishing was subjected to X-ray analysis of a particle cross-section using an X-ray microprobe (EPMA). The results are shown in FIG. 1. As can be clear from FIG. 1, the supported composite particle material had an outer layer substantially free of nickel and gold in a region at a depth of 0.5 μm from the outermost surface of the support, nickel and gold were supported in a region extending to a depth of 10 μm from the surface, and composite particles were confirmed not be present within the support.

Next, when the form of the above-mentioned supported composite particle material was observed with a transmission electron microscope (TEM/STEM), spherical nanoparticles extensively distributed within a particle diameter of 2 to 3 nm (number average particle diameter: 3.0 nm) was confirmed to be supported on the support. Observation of the nanoparticles under higher magnification revealed lattice fringe corresponding to the interplanar spacing of Au (111) in the nanoparticles. Compositional point analysis of individual nanoparticles by STEM-EDS indicated that nickel and gold were detected in all of the particles. The mean value of the atomic ratio of nickel/gold of the nanoparticles (calculated quantity: 50) was 1.05. Moreover, analysis of the nanoregions of the observed particles revealed the Ni/Au atomic ratio in the central portions of the particles to be 0.90, while that on the edges of the particles was 2.56. Trace amounts of nickel only were detected in portions other than the particles. As a result of carrying out fifty similar measurements, nickel was detected in large amounts in the edges of all particles. The distribution of nickel and gold was observed to be nearly consistent based on the results of EDS elementary mapping. In addition, the magnitude of the distribution of nickel was found to be one level greater than that of the distribution of gold in all scanning direction based on the results of compositional line profiles.

Based on the results of powder X-ray diffraction (XRD), a diffraction pattern attributable to nickel was not observed, and nickel was confirmed to be present in an amorphous state. On the other hand, although not well-defined, a broad peak was present corresponding to gold crystals. Although the value is close to the detection limit of powder X-ray diffraction (2 nm), the mean crystallite diameter thereof was about 3 nm as calculated according to the Scherrer equation. With respect to the chemical state of nickel, nickel was confirmed to be bivalent based on the results of X-ray photoelectron spectroscopy (XPS).

The chemical state of nickel was also predicted to be such that the nickel was in a high-spin state and have a valence of 2 based on the results of high-resolution X-ray fluorescence (HRXRF), and was determined to have a different chemical state than a single compound in the form of nickel oxide due to differences in the Ni Kα spectra. The half-width value (FWHM) of the Ni Kα spectrum of the resulting catalyst based on the measured spectrum was 3.470 and the chemical shift (ΔE) was 0.335. The half-width value (FHWM) of the Ni Kα spectrum of nickel oxide measured as a reference substance was 3.249 while the chemical shift (ΔE) was 0.344.

In addition, as a result of investigating changes in electron excitation states of the supported composite particle material by ultraviolet-visible spectroscopy (UV-Vis), a surface plasmon absorption peak originating from gold nanoparticles did not appear in the vicinity of 530 nm, while broad absorption attributable to NiO$_2$ was observed in the wavelength range of 200 to 800 nm.

On the basis of these results, the microstructure of the composite particles was predicted to have a form in which the surfaces of gold nanoparticles are covered by oxidized nickel.

Example 2

1.0 L of an aqueous solution in which was dissolved 2.90 g of magnesium chloride was heated to 80° C. and stirred followed by the addition of 300 g of the support obtained in the Support Production Reference Example and further stirring for 15 minutes at 80° C. Next, an aqueous solution containing 37.16 g of nickel nitrate hexahydrate and 35 mL of a 2.0 mol/L aqueous solution of palladium chloride was prepared followed by adding that heated to 80° C. to the above-mentioned support slurry and continuing to stir for 30 minutes at 80° C. to insolubly fix the nickel and palladium component on the support.

Next, after removing the supernatant by allowing to stand undisturbed and washing several times with distilled water, the washed supernatant was filtered. After drying for 10 hours at 105° C., the product was fired for 5 hours at 500° C. in air. Next, the supported material thus obtained was subjected to reducing treatment at room temperature for 2 hours in a hydrogen atmosphere to obtain a supported composite particle material (NiOPd/α-alumina) supported with 2.48% by mass of nickel and 2.30% by mass of palladium. The atomic ratio of Ni/(Ni+Pd) of the supported material thus obtained was 0.66.

Figure 2:
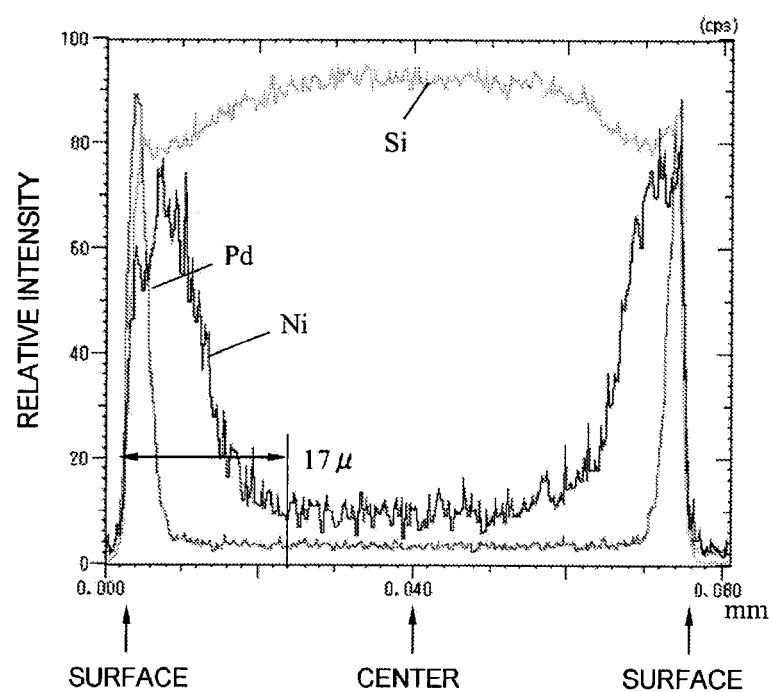
FIG. 2 shows the results of X-ray analysis using an X-ray microprobe of a particle cross-section of the supported composite particle material of Example 2.

A sample obtained by embedding the resulting supported composite particle material in resin and polishing was subjected to X-ray analysis of a particle cross-section using an X-ray microprobe (EPMA). The results are shown in FIG. 2. As can be clear from FIG. 2, nickel and palladium were confirmed to be supported in a region at a depth of 17 μm from the support surface while being absent inside.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to palladium crystals. The mean crystallite diameter thereof was about 5 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 4 to 5 nm (number average particle diameter: 4.8 nm) were confirmed to be supported on the support. Elementary analyses (20 points) were then carried out on individual observed nanoparticles with the energy dispersive X-ray detector (EDX) provided, and nickel and palladium were confirmed to be contained in all particles. The atomic ratio of nickel/palladium (mean value) of these composite particles was 0.8.

Example 3

1.0 L of an aqueous solution in which was dissolved 3.66 g of aluminum nitrate nonahydrate was heated to 80° C. and stirred followed by the addition of 300 g of the support obtained in the Support Production Reference Example and further stirring for 10 minutes at 80° C. Next, an aqueous solution containing 25.78 g of nickel nitrate hexahydrate and 37 mL of a 1.3 mol/L aqueous solution of chloroauric acid was prepared followed by adding that heated to 80° C. to the above-mentioned support slurry and continuing to stir for 15 minutes at 80° C. to insolubly fix the nickel and gold component on the support.

Next, after removing the supernatant by allowing to stand undisturbed and washing several times with distilled water, the washed supernatant was filtered. After drying for 10 hours at 105° C., the product was fired for 5 hours at 400° C. in an air to obtain a supported composite particle material (NiOAu/$SiO_2$—$Al_2O_3$—MgO) supported with 2.20% by mass of nickel and 1.96% by mass of gold. The atomic ratio of Ni/(Ni+Au) of the supported material thus obtained was 0.79.

A sample obtained by embedding the resulting supported composite particle material in resin and polishing was subjected to X-ray analysis of a particle cross-section using an X-ray microprobe (EPMA). As a result, the supported composite particle material was confirmed to have an outer layer substantially free of nickel and gold in a region extending to a depth of 2.0 μm from the outermost surface of the support, and nickel and gold were supported in a region extending to a depth of 15 μm from the surface, while being absent inside.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to gold crystals. The mean crystallite diameter thereof was about 4 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 3 to 4 nm (number average particle diameter: 3.8 nm) were confirmed to be supported on the support. Elementary analyses (20 points) were then carried out on individual observed nanoparticles with the energy dispersive X-ray detector (EDX) provided, and nickel and gold were confirmed to be contained in all particles. The atomic ratio of nickel/gold (mean value) of these composite particles was 1.10.

Example 4

A supported composite particle material (NiOAu/$SiO_2$—$Al_2O_3$—MgO) supported with 1.02% by mass of nickel and 0.89% by mass of gold was obtained by preparing in the same manner as Example 1 with the exception of not aging the support and stirring the support slurry and aqueous solution containing nickel and gold for 15 minutes at 60° C. The atomic ratio of Ni/(Ni+Au) of the supported material thus obtained was 0.79.

A sample obtained by embedding the resulting supported composite particle material in resin and polishing was subjected to X-ray analysis of a particle cross-section using an X-ray microprobe (EPMA). As a result, nickel and gold were confirmed to be supported in a region extending to a depth of 25 μm from the support surface, while being absent inside.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to gold crystals. The mean crystallite diameter thereof was about 3 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 3 to 4 nm (number average particle diameter: 3.5 nm) were confirmed to be supported on the support. Elementary analyses (20 points) were then carried out on individual observed nanoparticles with the energy dispersive X-ray detector (EDX) provided, and nickel and gold were confirmed to be contained in all particles. The atomic ratio of nickel/gold (mean value) of these composite particles was 1.02.

Example 5

A commercially available silica (Fuji Silysia Chemical, Cariact Q-10, particle diameter: 150 μm) was impregnated with 4% by mass of lanthanum followed by firing in air for 5 hours at 600° C. Next, 1.0 L of an aqueous solution in which was dissolved 8.91 g of aluminum nitrate nonahydrate was heated to 70° C. and stirred followed by the addition of 300 g of the above-mentioned silica support and further stirring for 30 minutes at 70° C. Next, an aqueous solution containing 17.84 g of nickel nitrate hexahydrate and 14 mL of a 1.3 mol/L aqueous solution of chloroauric acid was prepared followed by the addition of that heated to 70° C. to the support slurry and further continuing to stir for 30 minutes at 70° C. to insolubly fix the nickel and gold component on the support.

Next, after removing the supernatant by allowing to stand undisturbed and washing several times with distilled water, the washed supernatant was filtered. After drying for 10 hours at 105° C., the product was fired for 3 hours at 550° C. in air to obtain a supported composite particle material (NiOAu/$SiO_2$—$La_2O_3$) supported with 1.10% by mass of nickel and 1.02% by mass of gold. The atomic ratio of Ni/(Ni+Au) of the supported material thus obtained was 0.78.

A sample obtained by embedding the resulting supported composite particle material in resin and polishing was subjected to X-ray analysis of a particle cross-section using an X-ray microprobe (EPMA). As a result, the supported composite particle material was confirmed to have an outer layer substantially free of nickel and gold in a region extending to a depth of 5.0 μm from the outermost surface of the support, and nickel and gold were supported in a region extending to a depth of 30 μm from the surface, while being absent inside.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to gold crystals. Although close to the detection limit of powder X-ray diffraction (2 nm, the mean crystallite diameter thereof was about 3 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 2 to 3 nm (number average particle diameter: 3.2 nm) were confirmed to be supported on the support. Elementary analyses (20 points) were then carried out on individual observed nanoparticles with the energy dispersive X-ray detector (EDX) provided, and nickel and gold were confirmed to be contained in all particles. The atomic ratio of nickel/gold (mean value) of these composite particles was 1.02.

Example 6

A commercially available spherical alumina (Sumitomo Chemical, KHD, particle diameter: 3 mm) was impregnated with 5% by mass of potassium followed by firing in air for 5 hours at 600° C. Next, 300 g of the resulting alumina support was dispersed in 1.0 L of water heated to 90° C. and stirred for 15 minutes at 90° C. Next, an aqueous solution containing 38.65 g of nickel nitrate hexahydrate and 30 mL of a 1.3 mol/L aqueous solution of chloroauric acid was prepared followed by the addition of that heated to 90° C. to the support slurry and further continuing to stir for 30 minutes at 90° C. to insolubly fix the nickel and gold component on the support.

Next, after removing the supernatant by allowing to stand undisturbed and washing several times with distilled water, the washed supernatant was filtered. After drying for 10 hours at 105° C., the product was fired for 5 hours at 400° C. in air to obtain a supported composite particle material (NiOAu/ $Al_2O_3$—K) supported with 2.50% by mass of nickel and 2.46% by mass of gold. The atomic ratio of Ni/(Ni+Au) of the supported material thus obtained was 0.77.

A sample obtained by embedding the resulting supported composite particle material in resin and polishing was subjected to X-ray analysis of a particle cross-section using an X-ray microprobe (EPMA), and measurement of the distribution of nickel and gold was able to confirm that nickel and gold were supported in a region extending to 50 μm from the surface of the support, while being absent inside.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to gold crystals. The mean crystallite diameter thereof was about 4 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 3 to 4 nm (number average particle diameter: 3.6 nm) were confirmed to be supported on the support. Elementary analyses (20 points) were then carried out on individual observed nanoparticles with the energy dispersive X-ray detector (EDX) provided, and nickel and gold were confirmed to be contained in all particles. The atomic ratio of nickel/gold (mean value) of these composite particles was 0.94.

Comparative Example 1

1.0 L of an aqueous solution containing 16.35 g of nickel nitrate hexahydrate and 12 ml of a 1.3 mol/L aqueous solution of chloroauric acid was heated to 40° C. A supported composite particle material (NiOAu/$SiO_2$—$Al_2O_3$—MgO) supported with 1.07% by mass of nickel and 0.90% by mass of gold was obtained by preparing using the same procedure as Example 1 with the exception of adding 300 g of the support obtained in the Support Production Reference Example to this aqueous solution, continuing to stir for 30 minutes while holding at 40° C. and insolubly fixing the nickel and gold component on the support. The atomic ratio of Ni/(Ni+Au) of the supported material thus obtained was 0.80.

Figure 3:
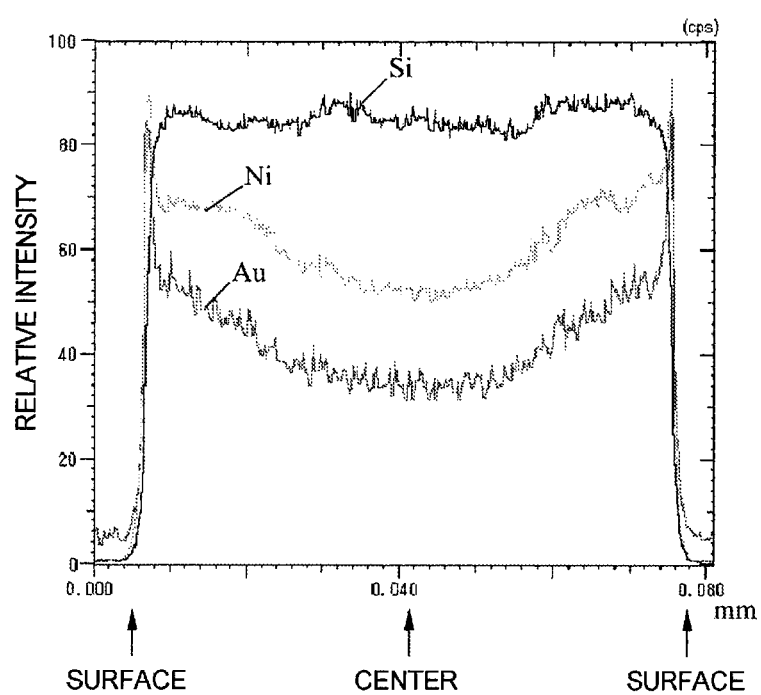
FIG. 3 shows the results of X-ray analysis using an X-ray microprobe of a particle cross-section of the supported composite particle material of Comparative Example 1.
Figure 4:
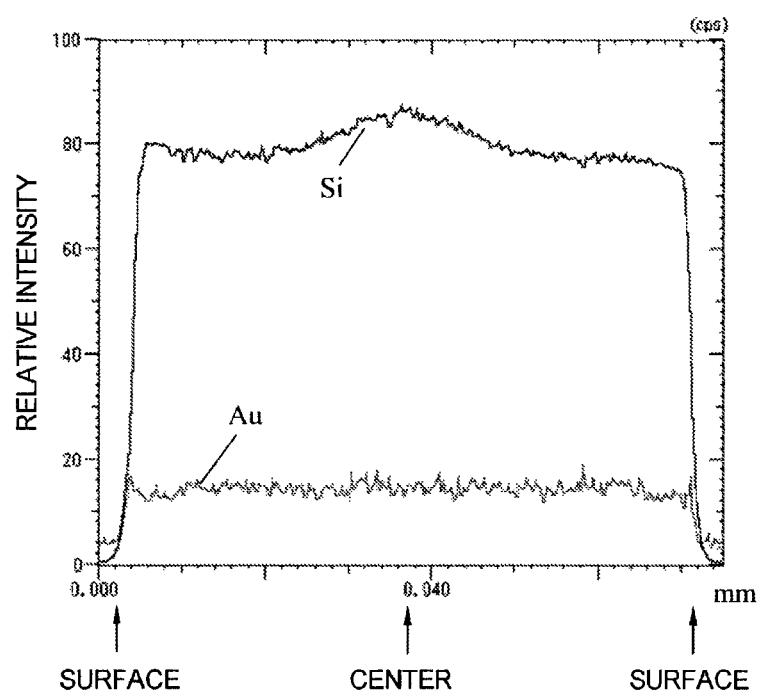
FIG. 4 shows the results of X-ray analysis using an X-ray microprobe of a particle cross-section of the supported composite particle material of Comparative Example 2.

A sample obtained by embedding the supported material thus obtained in resin and polishing was subjected to X-ray analysis of a particle cross-section using an X-ray microprobe (EPMA). The results are shown in FIG. 3. On the basis of FIG. 3, nickel and gold can be seen to be supported by being uniformly distributed from the surface to the interior.

Next, based on the results of powder X-ray diffraction (XRD) of the supported composite particle material, a diffraction pattern attributable to nickel was not observed, and nickel was confirmed to be present in an amorphous state. On the other hand, although not well-defined, a broad peak was present corresponding to gold crystals. Although close to the detection limit of powder X-ray diffraction (2 nm), the mean crystallite diameter thereof was about 3 nm as calculated according to the Scherrer equation. With respect to the chemical state of Ni, nickel was confirmed to be bivalent based on the results of X-ray photoelectron spectroscopy (XPS).

In addition, when the state of active species of this supported material was observed with a transmission electron microscope (TEM/STEM), nanoparticles extensively distributed within a particle diameter of 2 to 3 nm (number average particle diameter: 3.2 nm) were confirmed to be supported on the support. Elementary analyses (20 points) were then carried out on individual observed nanoparticles with the energy dispersive X-ray detector (EDX) provided, and nickel and gold were confirmed to be contained in all particles. The atomic ratio of nickel/gold (mean value) of these composite particles was 0.97.

Comparative Example 2

A supported gold particle material (Au/$SiO_2$—$Al_2O_3$—MgO) supported with 0.90% by mass of gold was obtained by preparing a supported material using the same procedure as Example 1 with the exception of not adding nickel nitrate hexahydrate.

A sample obtained by embedding the resulting supported gold particle material in resin and polishing was subjected to X-ray analysis of a particle cross-section using an X-ray microprobe (EPMA). The results are shown in FIG. 5. On the basis of FIG. 5, gold can be seen to be supported by being uniformly distributed from the surface to the interior.

Next, based on the results of powder X-ray diffraction (XRD), a broad peak was present corresponding to gold crystals. The mean crystallite diameter thereof was about 3 nm as calculated according to the Scherrer equation. When the state of the supported gold particle material was observed with a transmission electron microscope (TEM), gold particles having a mean particle diameter of 2.9 nm were confirmed to be supported on the support. In addition, as a result of investigating the electron excitation state of this supported gold particle material by ultraviolet-visible spectroscopy (UV-Vis), a surface plasmon absorption peak originating from gold particles was observed (at about 530 nm).

Table 1 shows the physical properties of the supported composite particle material of Examples 1 to 6 and Comparative Examples 1 and 2.

TABLE 1

| No. | Supported Composite Particle Material | Support Particle Diameter | Adsorption Temperature (°C.) | Loading of Ni and X (%) Ni | Loading of Ni and X (%) X | Composite Particle Diameter (nm) | Ni/X Atomic Ratio (mol/mol) | Composite Particle Distribution Region (μm) Composite Particle Layer | Composite Particle Distribution Region (μm) Outer Layer |
|---|---|---|---|---|---|---|---|---|---|
| Example 1 | NiOAu/SiO$_2$—Al$_2$O$_3$—MgO | 60 μm | 90 | 1.05 | 0.91 | 3 | 1.05 | 10 | 0.5 |
| Example 2 | NiOPd/SiO$_2$—Al$_2$O$_3$—MgO | 60 μm | 80 | 2.48 | 2.3 | 4.8 | 0.8 | 17 | — |
| Example 3 | NiOAu/SiO$_2$—Al$_2$O$_3$—MgO | 60 μm | 80 | 2.2 | 1.96 | 3.8 | 1.1 | 15 | 3 |
| Example 4 | NiOAu/SiO$_2$—Al$_2$O$_3$—MgO | 60 μm | 60 | 1.02 | 0.89 | 3.5 | 1.02 | 25 | — |
| Example 5 | NiOAu/SiO$_2$—La$_2$O$_3$ | 150 μm | 70 | 1.1 | 1.02 | 3.2 | 1.02 | 30 | 5 |
| Example 6 | NiOAu/Al$_2$O$_3$—K | 3 mm | 90 | 2.5 | 2.46 | 3.6 | 0.94 | 50 | — |
| Comp. Ex. 1 | NiOAu/SiO$_2$—Al$_2$O$_3$—MgO | 60 μm | 40 | 1.07 | 0.9 | 3.2 | 0.97 | Distributed inside | |
| Comp. Ex. 2 | Au/SiO$_2$—Al$_2$O$_3$—MgO | 60 μm | 90 | — | 0.9 | 2.9 | — | Distributed inside | |

Example 7

240 g of the supported composite particle material of Example 1 were charged into a stirred stainless steel reactor equipped with a catalyst separator and having a liquid phase portion of 1.2 liters, followed by carrying out a oxidative carboxylic acid ester formation reaction from aldehyde and alcohol while stirring the contents at a rate in terms of the stirrer tip speed of 4 m/s. A 36.7% by masst methacrolein/methanol solution at 0.6 liters/hr and a 1 to 4% by mass NaOH/methanol solution at 0.06 liters/hr were continuously supplied to the reactor, air was blown in at a reaction temperature of 80° C. and reaction pressure of 0.5 MPa so that the outlet oxygen concentration was 4.0% by volume (equivalent to oxygen partial pressure of 0.02 MPa), and the concentration of NaOH supplied to the reactor was controlled so that a pH of the reaction system was 7. The reaction product was continuously extracted from the reactor outlet by overflow and reactivity was investigated by analyzing by gas chromatography.

At 500 hours after the start of the reaction, the methacrolein conversion rate was 75.4%, the selection rate of methyl methacrylate was 97.2%, and the formation activity of methyl methacrylate based on the supported material unit mass was 9.568 mol/h/kg-cat. Reactivity after 2000 hours had elapsed indicated a methacrolein conversion rate of 75.1%, methyl methacrylate selection rate of 97.1% and methyl methacrylate formation activity of 9.520 mol/h/kg-cat, thus showing hardly any change in reactivity. When the supported composite particle material was recovered and the loading of nickel and gold after 2000 hours were compared with the initial loading thereof, the nickel and gold losses were 0.1% or less, respectively, thus confirming that separation and elution of active components in the form of nickel and gold was inhibited.

Next, when the recovered supported composite particle material was observed with a transmission electron microscope (TEM/STEM), composite particles extensively distributed within a particle diameter of 2 to 3 nm (number average particle diameter: 3.2 nm) were confirmed to be supported on the support. Compositional point analysis of individual composite particles by STEM-EDS confirmed that nickel and gold were contained in all of the particles. The mean value of the atomic ratio of nickel/gold of the composite particles (calculated quantity: 50) was 1.10. In addition, as a result of investigating changes in electron excitation states of the supported material by ultraviolet-visible spectroscopy (UV-Vis), a surface plasmon absorption peak originating from gold particles was not observed in the vicinity of 530 nm.

Comparative Example 3

A reaction was carried out under the same operating conditions as Example 1 using the supported composite particle material of Comparative Example 1. As a result, at 500 hours after the start of the reaction, the methacrolein conversion rate was 63.4%, the selection rate of methyl methacrylate was 95.8%, and the formation activity of methyl methacrylate based on the supported material unit mass was 6.608 mol/h/kg-cat. Reactivity after 2000 hours had elapsed indicated a methacrolein conversion rate of 58.7%, methyl methacrylate selection rate of 95.7% and methyl methacrylate formation activity of 6.111 mol/h/kg-cat, thus showing decreases in reaction activity and selectivity. When the supported composite particle material was recovered and the loading of nickel and gold after 2000 hours were compared with the initial loading thereof, the nickel and gold losses were 3.0% and 2.0%, respectively. The number average particle diameter of the composite particles as determined with a transmission electron microscope (TEM) was 3.8 nm, and sintering of composite particles was observed.

Comparative Example 4

A reaction was carried out under the same operating conditions as Example 1 using the supported composite particle material of Comparative Example 2. As a result, at 200 hours after the start of the reaction, the methacrolein conversion rate was 25.1%, the selection rate of methyl methacrylate was 81.5%, and the formation activity of methyl methacrylate based on the supported material unit mass was 2.671 mol/h/kg-cat. Reactivity after 700 hours had elapsed indicated a methacrolein conversion rate of 18.3%, methyl methacrylate selection rate of 79.1% and methyl methacrylate formation activity of 1.89 mol/h/kg-cat, thus showing decreases in reaction activity and selectivity. When the supported composite particle material was recovered and the loading of gold after 700 hours were compared with the initial loading thereof, the gold loss was 8.5%. The number average particle diameter of gold particles as determined with a transmission electron microscope (TEM) was 4.8 nm, and sintering of gold particles was observed.

On the basis of the above results, the supported composite particle material of the present embodiment was confirmed to maintain an extremely high level of reactivity for a long period of time and the structure of the composite particles thereof were confirmed to not change before and after the reaction in the case of using as a catalyst of a carboxylic acid ester formation reaction as previously described. Moreover, as a result of being provided with an outer layer substantially free of the composite particles, a supported composite particle material is obtained in which nickel and gold component loss caused by friction and the like can be inhibited. As observed in the previously described reaction examples, when composite particles are supported near the surface of the support, reaction activity increases and metal component loss decreases. Thus, in comparison with conventional supported materials, considerable improvement in economy can be obtained not only in this specific reaction, but also in general in a wider range of numerous other reactions.

The present application is based on a Japanese patent application filed with the Japanese Patent Office on Oct. 26, 2007 (Japanese Patent Application No. 2007-279397), the content of which is incorporated herein by reference.

INDUSTRIAL APPLICABILITY

The supported composite particle material according to the present invention has industrial applicability as a catalyst for chemical synthesis such as a carboxylic acid ester formation reaction between an aldehyde and an alcohol.

We claim:

1. A supported composite particle material comprising:
   a composite particle formed of an oxidized nickel and X (wherein X represents at least one of elements selected from the group consisting of palladium, platinum, ruthenium, gold and silver); and
   a support on which the composite particle is supported,
   wherein the supported composite particle material comprises a supported layer in which the composite particle is localized, and
   wherein the supported layer in which the composite particle is localized is present in a region extending from a surface of the supported composite particle material to 40% of an equivalent diameter of the supported composite particle material.

2. The supported composite particle material according to claim 1, wherein the equivalent diameter of the supported composite particle material exceeds 200 µm, and the supported layer in which the composite particle is localized is present in a region extending by 80 µm from an outer surface of the supported composite particle material.

3. The supported composite particle material according to claim 1, wherein the equivalent diameter of the supported composite particle material is 200 µm or less, and the supported layer in which the composite particle is localized is present in a region extending from the surface of the supported composite particle material to 30% of the equivalent diameter of the supported composite particle material.

4. The supported composite particle material according to claim 1, comprising an outer layer substantially free of the composite particle on an outside of the supported layer in which the composite particle is localized.

5. The supported composite particle material according to claim 4, wherein the outer layer is formed at a thickness of 0.01 to 15 µm from the outer surface of the support.

6. The supported composite particle material according to claim 1, wherein the composite particle has a mean particle diameter of from 2 to 10 nm.

7. The supported composite particle material according to claim 1, wherein a compositional ratio of nickel and X in the composite particle, in terms of an atomic ratio of Ni/X, is from 0.1 to 10.

8. The supported composite particle material according to claim 1, wherein the composite particle has a core formed of X and the core is coated with oxidized nickel.

9. The supported composite particle material according to claim 1, wherein the support is formed of an aluminum-containing silica-based composition containing silica and alumina.

10. A process for producing carboxylic acid ester comprising:
    reacting an aldehyde and an alcohol in the presence of oxygen by using the supported composite particle material according to claim 1 as a catalyst.

11. The process for producing carboxylic acid ester according to claim 10, wherein the aldehyde is selected from acrolein, methacrolein or a mixture thereof.

12. The process for producing carboxylic acid ester according to claim 10, wherein the alcohol is methanol.

13. A process for producing a supported composite particle material in which the composite particle formed of an oxidized nickel and X (wherein X represents at least one of elements selected from the group consisting of palladium, platinum, ruthenium, gold and silver) is supported onto a support, comprising:
    a first step of obtaining a mixture at a temperature of at least 60° C. by mixing an aqueous slurry containing a support on which is supported an oxide of at least one of basic metals selected from the group consisting of alkaline metals, alkaline earth metals and rare earth metals, and an acidic aqueous solution of a soluble metal salt containing nickel and the X; and
    a second step of heat-treating a precursor contained in the mixture.

14. The process for producing the supported composite particle material according to claim 13, wherein the aqueous slurry further comprises a salt of at least one of basic metals selected from the group consisting of alkaline metals, alkaline earth metals and rare earth metals.

15. The process for producing the supported composite particle material according to claim 13 or 14, wherein the aqueous slurry further comprises a soluble aluminum salt.

* * * * *